United States Patent [19]

Naya

[11] Patent Number: 5,923,031
[45] Date of Patent: Jul. 13, 1999

[54] SURFACE PLASMON SENSOR HAVING A COUPLER WITH A REFRACTIVE INDEX MATCHING LIQUID

[75] Inventor: Masayuki Naya, Kanagawa-ken, Japan

[73] Assignee: Fuji Photo Film Co., Ltd., Kanagawa-Ken, Japan

[21] Appl. No.: 09/018,332

[22] Filed: Feb. 4, 1998

[30] Foreign Application Priority Data

| Feb. 7, 1997 | [JP] | Japan | 9-025037 |
| Feb. 26, 1997 | [JP] | Japan | 9-041952 |
| Feb. 26, 1997 | [JP] | Japan | 9-041953 |
| May 27, 1997 | [JP] | Japan | 9-136530 |
| Jun. 6, 1997 | [JP] | Japan | 9-149442 |
| Sep. 29, 1997 | [JP] | Japan | 9-264087 |

[51] Int. Cl.$^6$ ............................................. H01J 5/16
[52] U.S. Cl. ........................................ 250/227.25; 356/244
[58] Field of Search ........................ 250/227.25, 227.24, 250/227.14, 216; 356/244, 440, 445

[56] References Cited

U.S. PATENT DOCUMENTS

| 5,035,863 | 7/1991 | Finlan et al. | 422/82.05 |
| 5,164,589 | 11/1992 | Sjodin | 250/227.24 |

FOREIGN PATENT DOCUMENTS

| 0 341 928 | 11/1989 | European Pat. Off. . |
| 0 390 192 | 10/1990 | European Pat. Off. . |
| 9-292335 | 11/1997 | Japan . |
| 2 197 068 | 5/1988 | United Kingdom . |
| WO 90/05305 | 5/1990 | WIPO . |
| WO 92/05426 | 4/1992 | WIPO . |

OTHER PUBLICATIONS

J.D. Richards et al: "Surface–Plasmon Excitation Using a Polarization–Preserving Optical Fiber and an Index–matching fluid optical cell", Jun. 1, 1993, *Applied Optics*, vol. 32, NR. 16, pp. 2901–2906.

*Primary Examiner*—Que T. Le
*Attorney, Agent, or Firm*—Sughrue, Mion, Zinn, Macpeak & Seas, PLLC

[57] ABSTRACT

A surface plasmon sensor comprises a sensor unit, which is provided with a transparent substrate and a metal film, and a coupler, which carries out light beam coupling and is separate from the sensor unit. A light beam is entered from a light beam entry portion of the coupler, and an attenuated total reflection angle $\theta_{sp}$ is detected from the light beam, which has been totally reflected from an interface between the transparent substrate and the metal film and has then been radiated out of a light beam radiating portion of the coupler. The sensor unit is supported by a sensor unit attachment such that a distance between the transparent substrate and the coupler may be kept to be equal to a predetermined value. The space between the transparent substrate and the coupler is filled with a refractive index matching liquid. Fitting of the sensor unit in the surface plasmon sensor is easy to carry out, and the relationship between positions of the sensor unit and the coupler can be kept constant.

46 Claims, 17 Drawing Sheets

F I G.1
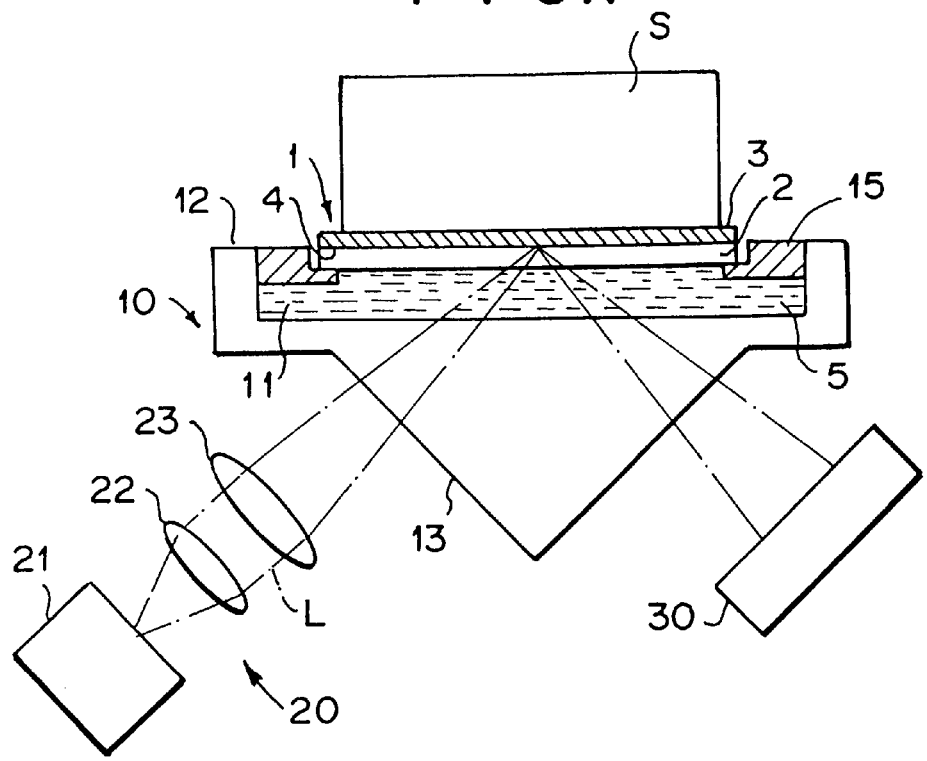
F I G.2
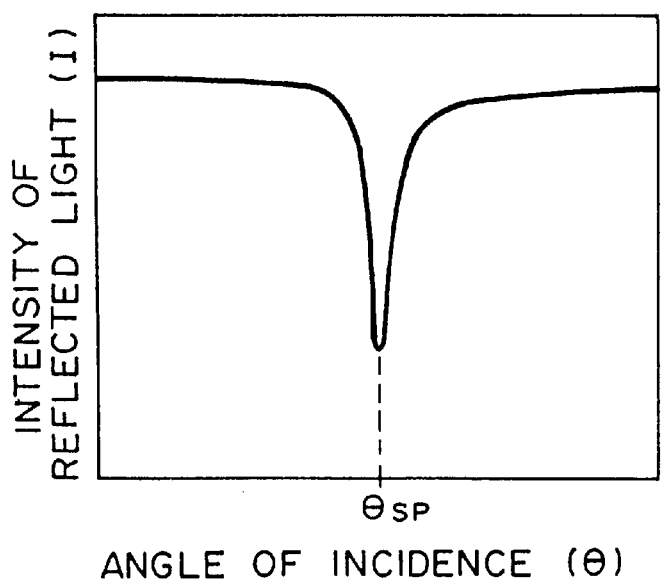

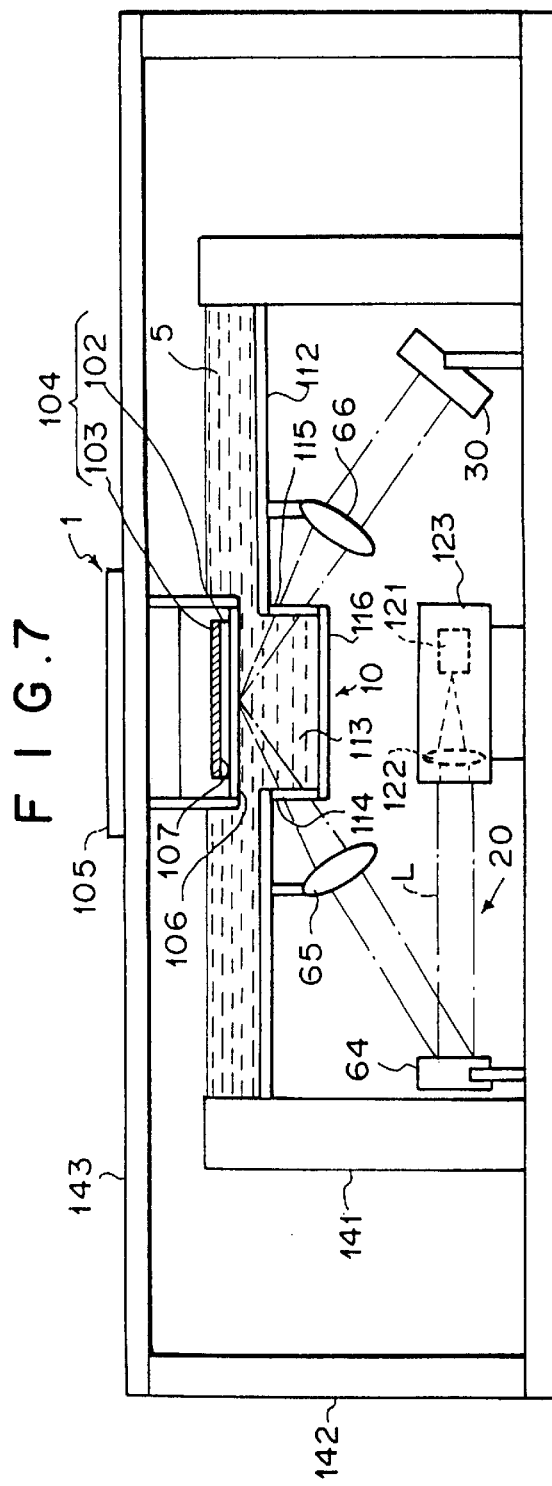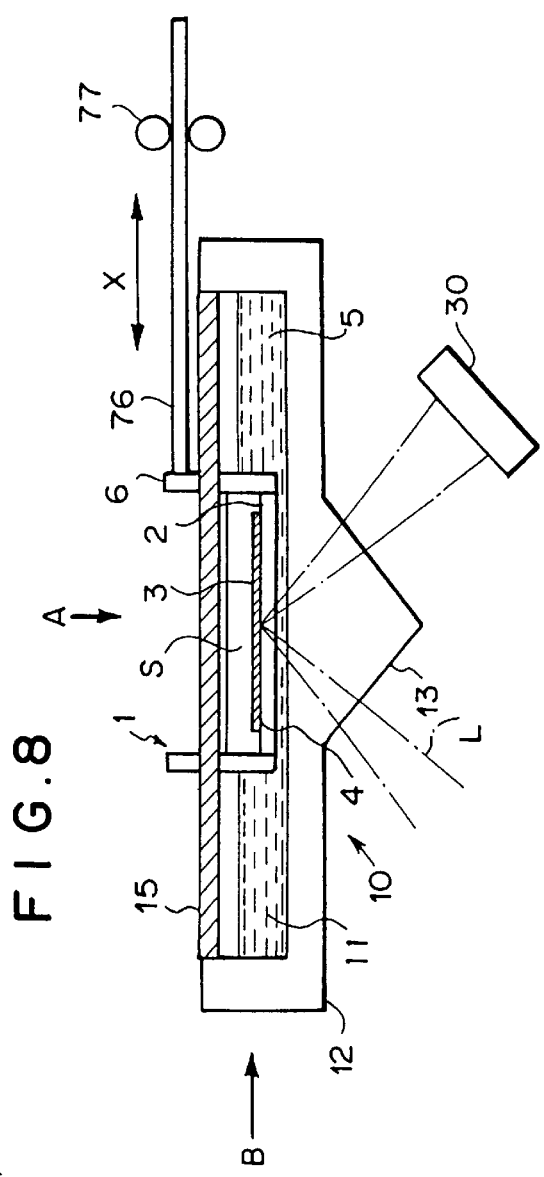

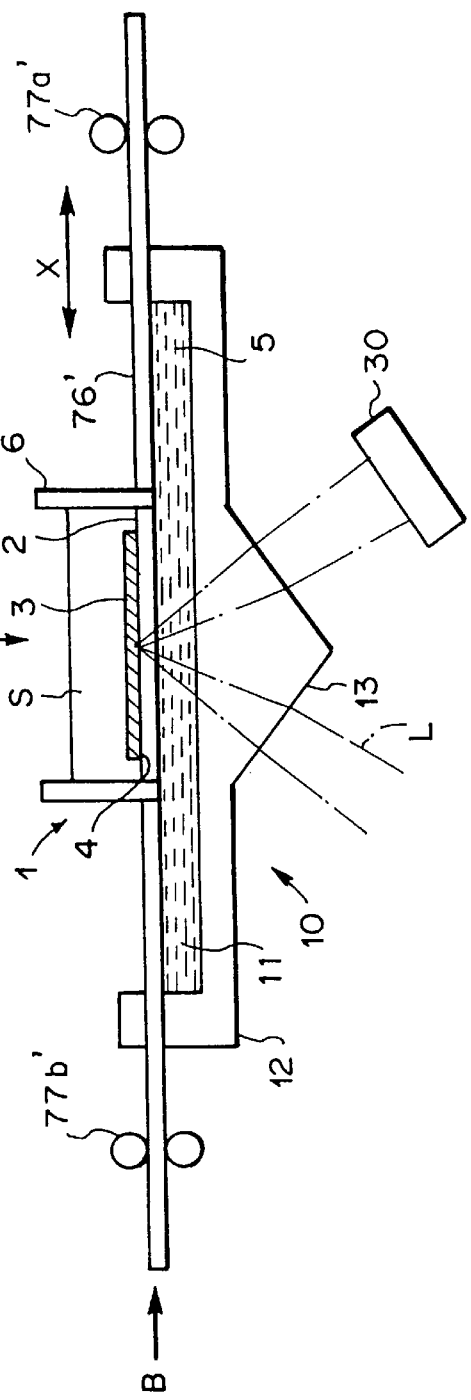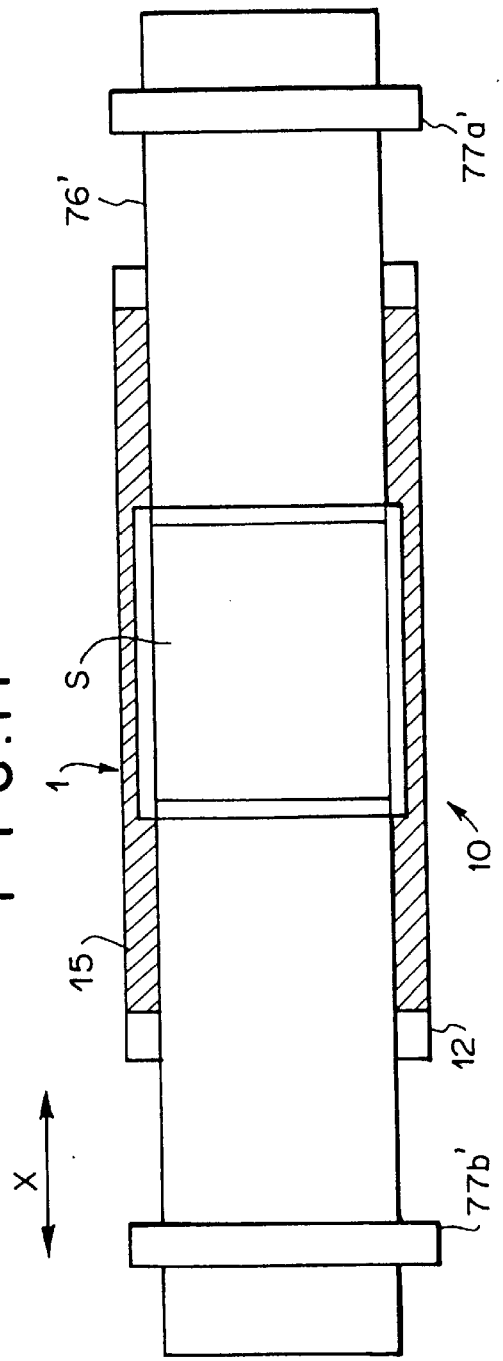

F I G. 15
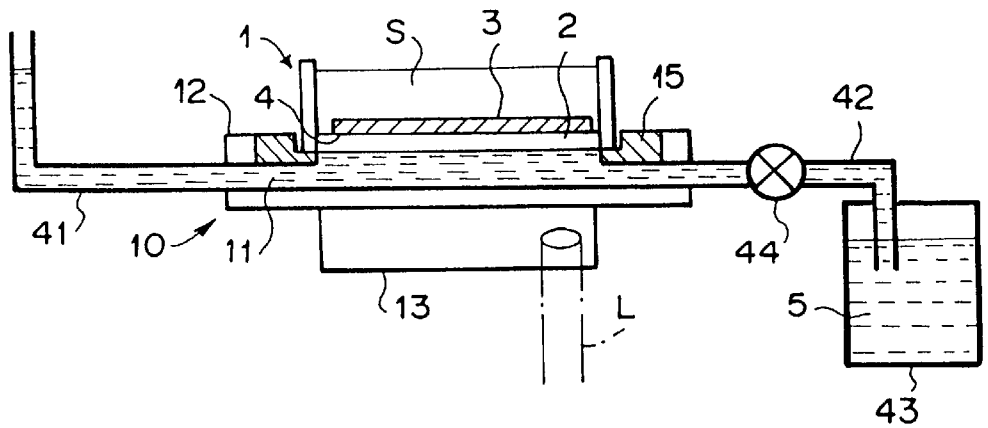
F I G. 16
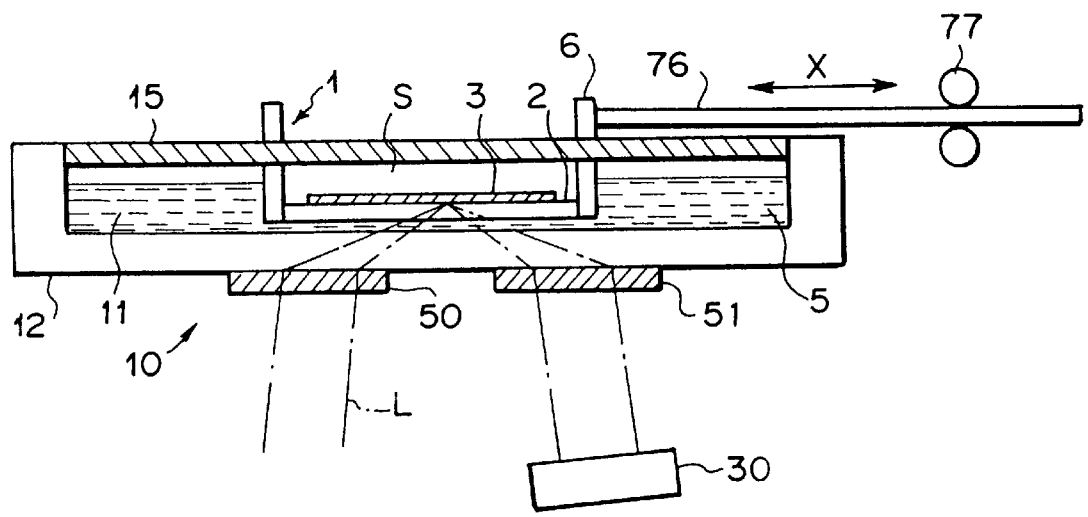
F I G. 17
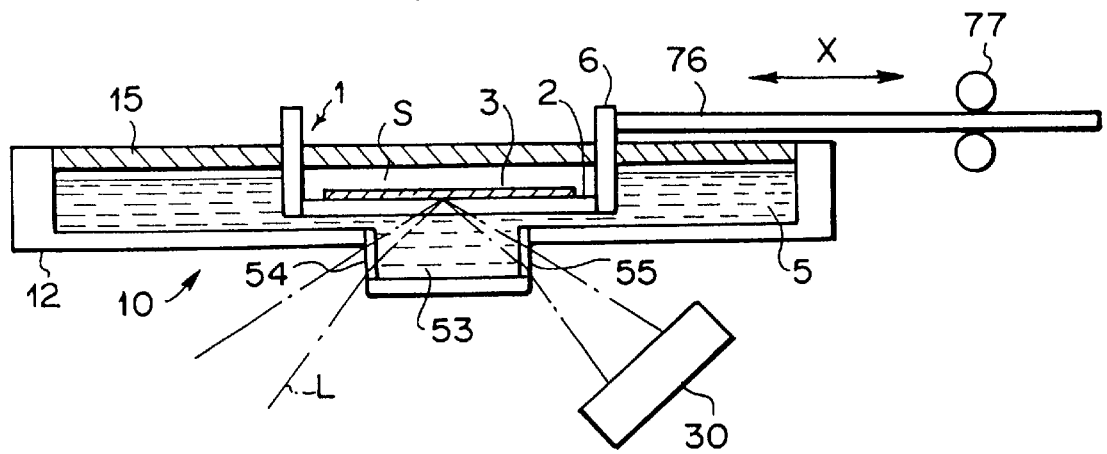

F I G. 19
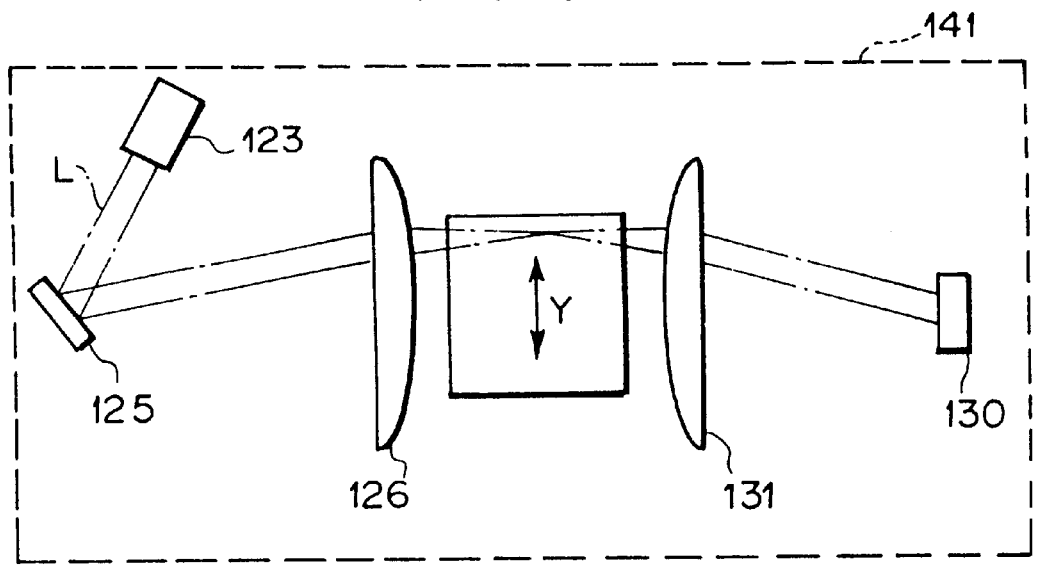
F I G. 20
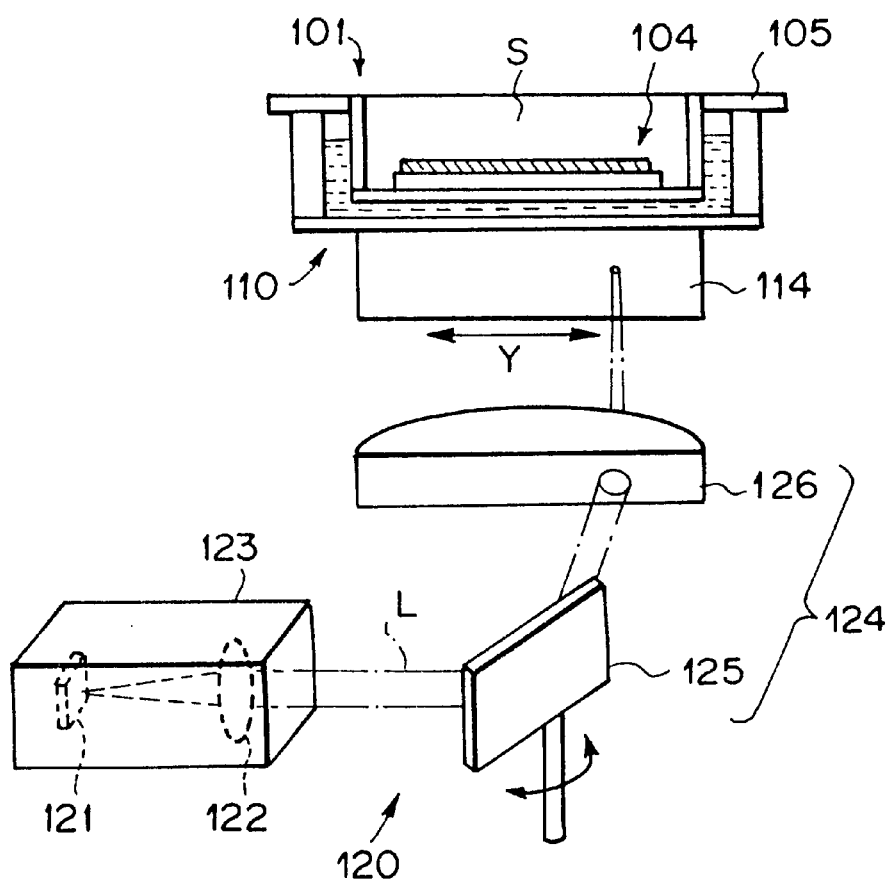

F I G. 25
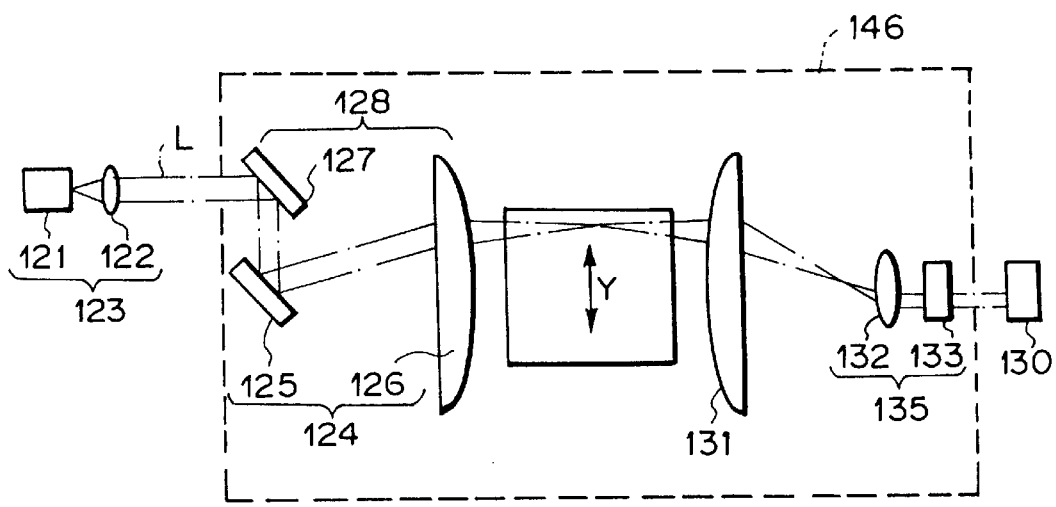

SURFACE PLASMON SENSOR HAVING A COUPLER WITH A REFRACTIVE INDEX MATCHING LIQUID

BACKGROUND OF THE INVENTION

1. Field of the Invention

This invention relates to a surface plasmon sensor for quantitatively analyzing a substance in a sample by utilizing the occurrence of surface plasmon. This invention particularly relates to a surface plasmon sensor, wherein a light beam coupler means and a metal film, which serves as a sensing means, are spaced apart from each other. This invention also relates to a surface plasmon sensor, which enables measurement with one- or two-dimensional scanning. This invention further relates to a surface plasmon sensor provided with an improved light beam coupler means.

2. Description of the Prior Art

In metals, free electrons vibrate collectively, and a compression wave referred to as a plasma wave is thereby produced. The compression wave occurring on the metal surface and having been quantized is referred to as the surface plasmon.

Various surface plasmon sensors for quantitatively analyzing a substance in a sample by utilizing a phenomenon, in which the surface plasmon is excited by a light wave, have heretofore been proposed. As one of well known surface plasmon sensors, a surface plasmon sensor utilizing a system referred to as the Kretschman arrangement may be mentioned. The surface plasmon sensor utilizing the system referred to as the Kretschman arrangement is described in, for example, Japanese Unexamined Patent Publication No. 6(1994)-167443.

Basically, the surface plasmon sensor utilizing the system referred to as the Kretschman arrangement comprises (i) a prism, (ii) a metal film, which is formed on one surface of the prism and is brought into contact with a sample, (iii) a light source for producing a light beam, (iv) an optical system for causing the light beam to pass through the prism and to impinge upon the interface between the prism and the metal film such that various different angles of incidence may be obtained with respect to the interface, and (v) a photo detecting means capable of detecting the intensity of the light beam, which has been totally reflected from the interface, with respect to each of the various different angles of incidence.

In order for various different angles of incidence to be obtained, a goniometer, with which a light beam irradiating system is rotated, may be employed. The goniometer is disclosed in, for example, Japanese Unexamined Patent Publication No. 6(1994)-50882. Alternatively, an optical system may be employed, with which a light beam having a comparatively large beam diameter is converged on the interface between the prism and the metal film such that the light beam may contain components impinging at various different angles of incidence upon the interface. In the former case, the light beam, which has been reflected at various different angles of reflection from the interface in accordance with the deflection of the incident light beam, may be detected with a small photodetector, which moves in synchronization with the deflection of the light beam, or may be detected with an area sensor extending in the direction, along which the angle of reflection of the light beam changes. In the latter case, the light beam may be detected with an area sensor extending in a direction such that the area sensor can receive all of the light beam components having been reflected at various different angles of reflection from the interface.

When a light beam impinges at an angle of incidence $\theta$, which is not smaller than the total reflection angle, upon the metal film, an oozing wave, which is referred to as an evanescent wave, occurs in the metal film serving as the reflection surface. The evanescent wave has an electric field distribution in the sample, which is in contact with the metal film, and the surface plasmon occurs at the interface between the metal film and the sample. In cases where the wave vector of the evanescent wave, which has occurred when the light beam composed of a P-polarized light component impinges upon the metal film, coincides with the wave vector of the surface plasmon and wave number matching is obtained, the evanescent wave and the surface plasmon resonate, and energy of the light transfers to the surface plasmon. As a result, the surface plasmon is excited. At this time, the intensity of the light, which is totally reflected from the metal film, becomes markedly low due to the transfer of light energy.

Therefore, with the surface plasmon sensor described above, the light beam is caused to impinge upon the metal film at various different angles of incidence $\theta$. Also, with respect to each of the various different angles of incidence $\theta$, the intensity of the light beam, which has been totally reflected from the metal film, is detected. In this manner, an angle of incidence $\theta_{sp}$ (hereinbelow referred to as the attenuated total reflection angle or the ATR angle) at which the phenomenon of marked decrease in intensity of reflected light beam occurs, can be found. A resonance wave number $K_{sp}$ can then be derived from ATR angle $\theta_{sp}$ and the wave vector $K_1$ of the incident light in accordance with the relationship, $K_{sp} = K_1 \sin\theta_{sp}$. If the wave number $K_{sp}$ of the surface plasmon is found, a dielectric constant of the sample can be calculated. Specifically, the formula shown below obtains.

$$K_{sp}(\omega) = \frac{\omega}{c}\sqrt{\frac{\varepsilon_m(\omega)\cdot\varepsilon_s}{\varepsilon_m(\omega)+\varepsilon_s}}$$

wherein $\omega$ represents the angular frequency of the surface plasmon, c represents the light velocity in a vacuum, $\varepsilon_m$ represents the dielectric constant of the metal, and $\varepsilon_s$ represents the dielectric constant of the sample.

If the dielectric constant $\varepsilon_s$ of the sample is found, the concentration of a specific substance contained in the sample can be calculated from a predetermined calibration curve, or the like. Accordingly, the specific substance contained in the sample can be quantitatively analyzed by finding the ATR angle $\theta_{sp}$, at which the intensity of the reflected light beam becomes low.

In the example of the surface plasmon sensor described above, the metal film, which serves as the sensing means, is formed directly on one surface of the prism, which serves as the light beam coupler. However, actually, for reasons of apparatus constitution, the surface plasmon sensor has the constitution such that the metal film may be formed as a film independent of the coupler. Specifically, the metal film is formed on one surface of a transparent substrate, which may be constituted of glass. (The combination of the transparent substrate and the metal film formed on the transparent substrate will hereinbelow be referred to as the sensor unit.) Also, the other surface of the transparent substrate is brought into close contact with the coupler. Heretofore, in cases where such a separation type of constitution is employed, a refractive index matching liquid is coated on the joint area between the sensor unit and the coupler, and the sensor unit and the coupler are thereby brought into close contact with each other with the refractive index matching liquid intervening therebetween, such that the adverse effects of reflection and multiple reflection due to an air layer at the joint area may be eliminated.

However, with the constitution in which the refractive index matching liquid is coated on the joint area between the sensor unit and the coupler, and the sensor unit and the coupler are thereby brought into close contact with each other with the refractive index matching liquid intervening therebetween, the problems occur in that considerable time and labor are required to mount and dismount the sensor unit. Since the exchanging of the sensor unit is carried out very frequently, it is desired that the exchanging of the sensor unit can be carried out easily. Also, the thickness of the layer of the refractive index matching liquid between the coupler and the sensor unit cannot easily be kept to be equal to a predetermined value. Nonuniformity in thickness of the layer of the refractive index matching liquid, which nonuniformity occurs at the time of exchanging of the sensor unit, or the like, adversely affects the detection accuracy of the surface plasmon sensor.

SUMMARY OF THE INVENTION

The primary object of the present invention is to provide a surface plasmon sensor, wherein it is easy to fit a sensor unit in the surface plasmon sensor, and relationship between positions of the sensor unit and a coupler is kept constant.

Another object of the present invention is to provide a surface plasmon sensor, which has a simple constitution and in which one- or two-dimensional scanning is capable of being carried out over a wide area.

A further object of the present invention is to provide a surface plasmon sensor, wherein multiple reflection interference of light does not occur, the size of an optical system is kept small, and various angles of incidence of a light beam upon an interface are obtained with a simple optical system.

A still further object of the present invention is to provide a surface plasmon sensor, wherein various angles of incidence of a light beam upon an interface are obtained with a simple optical system, and one- or two-dimensional scanning is capable of being carried out, such that analyses of a plurality of samples may be carried out under the same conditions, or such that two-dimensional information representing physical properties of a substance contained in a sample may be obtained.

The present invention provides a first surface plasmon sensor, comprising:
i) a sensor unit provided with a transparent substrate, which has a predetermined refractive index, and a metal film, which is located on one surface side of the transparent substrate, and
ii) a coupler means located on the other surface side of the transparent substrate, which surface side is opposite to the one surface, with a refractive index matching liquid, which has a refractive index approximately equal to the predetermined refractive index, intervening between the transparent substrate and the coupler means,
the coupler means having a light beam entry portion, which is formed at a portion of the coupler means, and a light beam radiating portion, which is formed at a different portion of the coupler means, such that the coupler means may transmit a converged light beam having been entered from the light beam entry portion, may cause the transmitted light beam to impinge with a predetermined beam diameter upon an interface between the transparent substrate and the metal film, may transmit the light beam having been reflected from the interface, and may then radiate the reflected light beam out of the light beam radiating portion, portions of the coupler means, which transmit the light beam, having a refractive index approximately equal to the predetermined refractive index,
the surface plasmon sensor causing the light beam to enter from the light beam entry portion and detecting an attenuated total reflection angle (i.e. an ATR angle) $\theta_{sp}$ from the light beam, which has been totally reflected from the interface and has then been radiated out of the light beam radiating portion,
wherein a sensor unit support means is provided, the sensor unit support means supporting the sensor unit such that a distance between the transparent substrate and the coupler means may be kept to be equal to a predetermined value, and
wherein the space between the transparent substrate and the coupler means is filled with the refractive index matching liquid.

In the first surface plasmon sensor in accordance with the present invention, by way of example, the sensor unit support means may be secured to a portion of the coupler means.

Also, in order for the aforesaid space to be filled with the refractive index matching liquid, the constitution described below may be employed. Specifically, the first surface plasmon sensor in accordance with the present invention may further comprise a matching liquid supply means, which supplies the refractive index matching liquid into the space, and
a vacant member, which communicates with the space and allows the refractive index matching liquid to be introduced up to a position higher than the other surface of the transparent substrate,
the refractive index matching liquid being filled in the space by the matching liquid supply means.

Alternatively, a liquid reservoir for storing the refractive index matching liquid therein may be formed on the side of the coupler means, which side stands facing the transparent substrate,
the transparent substrate may be provided with a waterproof wall, which surrounds the metal film, and
the sensor unit may be supported in the liquid reservoir such that the other surface of the transparent substrate may be immersed in the refractive index matching liquid.

In this condition, the aforesaid space may be filled with the refractive index matching liquid.

The light beam entry portion and the light beam radiating portion of the coupler means may be formed in the manner described below. Specifically, the coupler means may be provided with a prism, and
the light beam entry portion and the light beam radiating portion may be formed in the prism.

Alternatively, each of the light beam entry portion and the light beam radiating portion of the coupler means may be constituted of a diffraction grating.

As another alternative, the coupler means may be provided with a convex portion on the side of the coupler means, which side is opposite to the side facing the transparent substrate,
each of one lateral face of the convex portion and the other lateral face thereof, which is opposite to the one lateral face, may be constituted of a transparent plate, the region inside of the convex portion being filled with the refractive index matching liquid, and the one lateral face and the other lateral face of the convex portion may respectively serve as the light beam entry portion and the light beam radiating portion.

The term "coupler means" as used herein means a group of various means for coupling the light beam, which impinges upon the interface between the transparent substrate and the metal film, under surface plasmon resonance producing conditions.

The first surface plasmon sensor in accordance with the present invention may be modified such that the transparent substrate of the sensor unit may be constituted of a main transparent substrate and a supporting transparent substrate, which have the predetermined refractive index and are in close contact with each other, the metal film may be located on the main transparent substrate, and the supporting transparent substrate may be located such that it may stand facing the coupler means with the refractive index matching liquid intervening therebetween.

Also, in such cases, the main transparent substrate and the supporting transparent substrate may be in close contact with each other via a refractive index matching liquid, which has a refractive index approximately equal to the predetermined refractive index.

Further, the first surface plasmon sensor in accordance with the present invention may be modified such that a bonding reaction film may be located on the metal film, and the surface plasmon sensor may detect a specific substance, which is capable of undergoing a bonding reaction with the bonding reaction film. By way of example, the "bonding reaction film" may be a film, to which an antigen (or an antibody) capable of undergoing an antigen-antibody reaction has been fixed, and the "specific substance capable of undergoing a bonding reaction with the bonding reaction film" may be the antibody (or the antigen).

The present invention also provides a second surface plasmon sensor, comprising:

i) a sensor unit provided with a transparent substrate, which has a predetermined refractive index, and a metal film, which is located on one surface side of the transparent substrate, and ii) a coupler means located on the other surface side of the transparent substrate, which surface side is opposite to the one surface, with a refractive index matching liquid, which has a refractive index approximately equal to the predetermined refractive index, intervening between the transparent substrate and the coupler means, the coupler means having a light beam entry portion, which is formed at a portion of the coupler means, and a light beam radiating portion, which is formed at a different portion of the coupler means, such that the coupler means may transmit a converged light beam having been entered from the light beam entry portion, may cause the transmitted light beam to impinge upon an interface between the transparent substrate and the metal film, may transmit the light beam having been totally reflected from the interface, and may then radiate the totally reflected light beam out of the light beam radiating portion, portions of the coupler means, which transmit the light beam, having a refractive index approximately equal to the predetermined refractive index, the surface plasmon sensor causing the light beam to enter from the light beam entry portion and detecting an ATR angle $\theta_{sp}$ from the light beam, which has been totally reflected from the interface and has then been radiated out of the light beam radiating portion, wherein a sensor unit support means is provided, the sensor unit support means supporting the sensor unit such that a distance between the transparent substrate and the coupler means may be kept to be equal to a predetermined value, wherein the space between the transparent substrate and the coupler means is filled with the refractive index matching liquid, and wherein the surface plasmon sensor further comprises either one or both of an incidence position shifting means and a sensor unit relative movement means, the incidence position shifting means shifting the incidence position of the light beam at the light beam entry portion such that the converged light beam may successively impinge upon different portions of the interface, which are taken along a predetermined direction, and under the same incidence conditions, the sensor unit relative movement means moving the sensor unit with respect to the coupler means and along a predetermined direction such that the distance between the transparent substrate and the coupler means may be kept to be equal to the predetermined value.

The second surface plasmon sensor in accordance with the present invention should preferably comprise both of the incidence position shifting means and the sensor unit relative movement means, and the predetermined direction, along which the different portions of the interface are taken in the shifting operation carried out by the incidence position shifting means, and the predetermined direction, along which the sensor unit is moved with respect to the coupler means by the sensor unit relative movement means, should preferably intersect with each other.

In the second surface plasmon sensor in accordance with the present invention, the incidence position shifting means may be means, such as a telecentric scanning optical system, in which the converged light beam is deflected by a light-source optical means provided with a galvanometer mirror, or the like, and the incidence position is thereby shifted. Alternatively, the incidence position shifting means may be means, in which a light-source optical means is moved mechanically, and the incidence position is thereby shifted.

Also, the sensor unit relative movement means for moving the sensor unit with respect to the coupler means may be a movement means, which moves the sensor unit itself. Alternatively, the sensor unit relative movement means for moving the sensor unit with respect to the coupler means may be a movement means, which moves the coupler means while the sensor unit is kept stationary.

In the second surface plasmon sensor in accordance with the present invention, by way of example, the sensor unit support means may be secured to a portion of the coupler means.

Alternatively, the second surface plasmon sensor in accordance with the present invention may be constituted such that a light-source optical means for producing the light beam and causing the light beam to enter into the light beam entry portion, a detection means for detecting an ATR angle $\theta_{sp}$ from the converged light beam having been radiated out of the light beam radiating portion, and the coupler means may be located on a base, the sensor unit support means may be located on the base and secured thereto, the sensor unit may be supported by the sensor unit support means such that the sensor unit can be moved with respect to the coupler means, and the sensor unit relative movement means may move the sensor unit.

As another alternative, the second surface plasmon sensor in accordance with the present invention may be constituted such that the sensor unit support means may be located on a base and secured thereto, the sensor unit may be fixedly supported by the sensor unit support means, an optical system unit may be located on the base such that the optical system unit can be moved with respect to the sensor unit, the optical system unit comprising a light-source optical means for producing the light beam and causing the light beam to enter into the light beam entry portion, a detection means for detecting an ATR angle $\theta_{sp}$ from the light beam having been radiated out of the light beam radiating portion, and the coupler means, and the sensor unit relative movement means may move the optical system unit.

As a further alternative, the second surface plasmon sensor in accordance with the present invention may be constituted such that the sensor unit support means may be located on a base and secured thereto, the sensor unit may be supported by the sensor unit support means such that the sensor unit can be moved with respect to the coupler means, the sensor unit relative movement means may move the sensor unit, an optical system unit may be located on the base, the optical system unit comprising an optical means for a light source, which optical means causes the light beam to enter into the light beam entry portion, an optical means for a detection means, which optical means guides the light beam to the detection means for detecting an ATR angle $\theta_{sp}$ from the light beam having been radiated out of the light beam radiating portion, and the coupler means, and the light source for producing the light beam and the detection means may be releasably located on the base and at positions independent of the optical system unit.

As a still further alternative, the second surface plasmon sensor in accordance with the present invention may be constituted such that the sensor unit support means may be located on a base and secured thereto, the sensor unit may be fixedly supported by the sensor unit support means, an optical system unit may be located on the base such that the optical system unit can be moved with respect to the sensor unit, the optical system unit comprising an optical means for a light source, which optical means causes the light beam to enter into the light beam entry portion, an optical means for a detection means, which optical means guides the light beam to the detection means for detecting an ATR angle $\theta_{sp}$ from the light beam having been radiated out of the light beam radiating portion, and the coupler means, the sensor unit relative movement means may move the optical system unit, and the light source for producing the light beam and the detection means may be releasably located on the base and at positions independent of the optical system unit.

As another alternative, the second surface plasmon sensor in accordance with the present invention may be constituted such that the sensor unit support means may be located on a base and secured thereto, the sensor unit may be supported by the sensor unit support means such that the sensor unit can be moved with respect to the coupler means, the sensor unit relative movement means may move the sensor unit, an optical system unit maybe located on the base, the optical system unit comprising an optical means for a light source, which optical means causes the light beam to enter into the light beam entry portion, a detection means for detecting an ATR angle $\theta_{sp}$ from the light beam having been radiated out of the light beam radiating portion, and the coupler means, and the light source for producing the light beam may be independently located at the exterior of the base.

As a further alternative, the second surface plasmon sensor in accordance with the present invention may be constituted such that the sensor unit support means may be located on a base and secured thereto, the sensor unit may be fixedly supported by the sensor unit support means, an optical system unit may be located on the base such that the optical system unit can be moved with respect to the sensor unit, the optical system unit comprising an optical means for a light source, which optical means causes the light beam to enter into the light beam entry portion, a detection means for detecting an ATR angle $\theta_{sp}$ from the light beam having been radiated out of the light beam radiating portion, and the coupler means, the sensor unit relative movement means may move the optical system unit, and the light source for producing the light beam may be independently located at the exterior of the base.

In the two last-described alternatives, the second surface plasmon sensor may be provided with an optical fiber for guiding the light beam, which has been produced by the light source, to the optical means for the light source. The optical fiber should preferably be of the polarization plane keeping type.

Further, in the second surface plasmon sensor in accordance with the present invention, in order for the aforesaid space to be filled with the refractive index matching liquid, the constitution described below may be employed. Specifically, the second surface plasmon sensor in accordance with the present invention may further comprise a matching liquid supply means, which supplies the refractive index matching liquid into the space, and a vacant member, which communicates with the space and allows the refractive index matching liquid to be introduced up to a position higher than the other surface of the transparent substrate, the refractive index matching liquid being filled in the space by the matching liquid supply means.

Alternatively, a liquid reservoir for storing the refractive index matching liquid therein may be formed on the side of the coupler means, which side stands facing the transparent substrate, the transparent substrate may be provided with a waterproof wall, which surrounds the metal film, and the sensor unit may be supported in the liquid reservoir such that the other surface of the transparent substrate may be immersed in the refractive index matching liquid.

In this condition, the aforesaid space may be filled with the refractive index matching liquid.

In the second surface plasmon sensor in accordance with the present invention, the light beam entry portion and the light beam radiating portion of the coupler means may be formed in the manner described below. Specifically, the coupler means maybe provided with a prism, and the light beam entry portion and the light beam radiating portion may be formed in the prism.

Alternatively, each of the light beam entry portion and the light beam radiating portion of the coupler means may be constituted of a diffraction grating.

As another alternative, the coupler means may be provided with a convex portion on the side of the coupler means, which side is opposite to the side facing the transparent substrate, each of one lateral face of the convex portion and the other lateral face thereof, which is opposite to the one lateral face, may be constituted of a transparent plate, the region inside of the convex portion being filled with the refractive index matching liquid, and the one lateral face and the other lateral face of the convex portion may respectively serve as the light beam entry portion and the light beam radiating portion.

The second surface plasmon sensor in accordance with the present invention may be modified such that the transparent substrate of the sensor unit may be constituted of a supporting transparent substrate and a main transparent substrate, which is located on the supporting transparent substrate, the metal film may be located on the main transparent substrate, and the supporting transparent substrate may be located such that it may stand facing the coupler means with the refractive index matching liquid intervening therebetween.

Alternatively, the transparent substrate of the sensor unit may be constituted of a supporting transparent substrate and a plurality of main transparent substrates, which are located at different positions on the supporting transparent substrate, the metal film may be located on each of the plurality of the main transparent substrates, and the supporting transparent substrate may be located such that it may stand facing the coupler means with the refractive index matching liquid intervening therebetween.

In such cases, the plurality of the main transparent substrates may have different substrate sizes. In cases where the transparent substrate of the sensor unit is constituted of the supporting transparent substrate and the main transparent substrate or the plurality of the main transparent substrates, the main transparent substrate and the supporting transparent substrate may be in close contact with each other via a refractive index matching liquid, which has a refractive index approximately equal to the predetermined refractive index. Also, the main transparent substrate should preferably be easily releasable from the supporting transparent substrate.

Furthermore, the second surface plasmon sensor in accordance with the present invention may be modified such that a bonding reaction film may be located on the metal film, and the surface plasmon sensor may detect a specific substance, which is capable of undergoing a bonding reaction with the bonding reaction film. By way of example, the "bonding reaction film" may be a film, to which an antigen (or an antibody) capable of undergoing an antigen-antibody reaction has been fixed, and the "specific substance capable of undergoing a bonding reaction with the bonding reaction film" may be the antibody (or the antigen). However, the bonding reaction film and the specific substance may be the ones capable of undergoing other chemical reactions. In cases where a plurality of main transparent substrates are provided, the bonding reaction films may be formed respectively on the metal films, which are located on the main transparent substrates. In such cases, the same kind of bonding reaction films, e.g. the bonding reaction films containing the same kind of antibody (or antigen), may be formed on the metal films. Alternatively, different kinds of bonding reaction films, e.g. the bonding reaction films containing different kinds of antibodies (or antigens), may be formed on the metal films. Also, the same kind of bonding reaction films or different kinds of bonding reaction films may be formed at different positions on a single metal film. In cases where a sensor unit provided with different kinds of bonding reaction films, e.g. the bonding reaction films containing different kinds of antibodies (or antigens), is employed, different phenomena occurring with a single sample at the respective bonding reaction films may be determined successively.

The present invention further provides a third surface plasmon sensor, comprising:

i) a sensor unit provided with a transparent substrate, which has a predetermined refractive index, and a metal film, which is located on one surface side of the transparent substrate and brought into contact with a sample, ii) a coupler means located on the other surface side of the transparent substrate, which surface side is opposite to the one surface, with a refractive index matching liquid, which has a refractive index approximately equal to the predetermined refractive index, intervening between the transparent substrate and the coupler means, the coupler means having a light beam entry portion, which is formed at a portion of the coupler means, and a light beam radiating portion, which is formed at a different portion of the coupler means, such that the coupler means may transmit a converged light beam having been entered from the light beam entry portion, may cause the transmitted light beam to impinge upon an interface between the transparent substrate and the metal film, may transmit the light beam having been totally reflected from the interface, and may then radiate the totally reflected light beam out of the light beam radiating portion, portions of the coupler means, which transmit the light beam, having a refractive index approximately equal to the predetermined refractive index, and iii) a light source for producing the light beam, the surface plasmon sensor collimating the light beam, which has been produced by the light source, causing the collimated light beam to enter from the light beam entry portion, and detecting an ATR angle $\theta_{sp}$ from the light beam, which has been totally reflected from the interface and has then been radiated out of the light beam radiating portion, wherein each of the light beam entry portion and the light beam radiating portion is constituted of a hologram optical element.

The third surface plasmon sensor in accordance with the present invention may be constituted such that the hologram optical element may be designed to converge the incident collimated light beam to a predetermined position, a light source moving means may be provided, the light source moving means moving the light source in a plane, which is parallel to the interface, and in a direction heading towards the predetermined position or in a direction heading away from the predetermined position, and the light source may be moved, whereby the light beam is caused to enter from different positions on the light beam entry portion and caused to impinge upon the interface at various different angles of incidence and at the predetermined position.

Also, in the third surface plasmon sensor in accordance with the present invention, the hologram optical element may have lens functions and aberration compensating functions, and the light beam may be converged to the predetermined position by the lens functions and the aberration compensating functions. Alternatively, the hologram optical element may have cylindrical lens functions and aberration compensating functions, and the light beam may be converged to the predetermined position by the cylindrical lens functions and the aberration compensating functions. In the former case, the aforesaid predetermined position is obtained as a point-like position. In the latter case, the aforesaid predetermined position is obtained as a linear position.

Specifically, the term "lens functions" as used herein means the functions for converging the incident light beam to a single point. Also, the term "cylindrical lens functions" as used herein means the functions having a refractive index in only one direction and converging the incident light beam with respect to the only one direction.

Further, the third surface plasmon sensor in accordance with the present invention may further comprise a position regulating means for regulating the position of the sensor unit such that a distance between the transparent substrate and the coupler means may be kept to be equal to a predetermined value, and a sensor unit moving means for moving the sensor unit in a predetermined direction, and the space between the transparent substrate and the coupler means may be filled with the refractive index matching liquid.

Furthermore, the third surface plasmon sensor in accordance with the present invention may further comprise an incidence position shifting means for shifting the incidence position of the light beam at the light beam entry portion such that the light beam may successively impinge upon different portions of the interface, which are taken along the same direction as an axial direction of the cylindrical lens functions.

The term "axial direction of cylindrical lens functions" as used herein means the direction of an axis that is normal to the plane, in which the cylindrical lens functions have the refracting power. The different portions of the interface, which are taken along the same direction as the axial direction of the cylindrical lens functions, are not limited to the portions along the axial direction, and it is sufficient for the portions to have a change in position along the axial direction.

In cases where the third surface plasmon sensor in accordance with the present invention is provided with both of the sensor unit moving means and the incidence position shifting means, the predetermined direction, along which the sensor unit is moved, and the axial direction of the cylindrical lens functions should preferably intersect with each other.

In the third surface plasmon sensor in accordance with the present invention, the incidence position shifting means may be constituted such that the light beam may be deflected by an optical system provided with a galvanometer mirror, or the like, and the incidence position may thereby be shifted. Alternatively, the incidence position shifting means maybe constituted such that the light source itself may be moved mechanically, and the incidence position may thereby be shifted.

The first surface plasmon sensor in accordance with the present invention is provided with the sensor unit support means for supporting the sensor unit, which is provided with the transparent substrate and the metal film located on one surface side of the transparent substrate and brought into contact with a sample, such that the distance between the transparent substrate and the coupler means may be kept to be equal to the predetermined value. Also, the space between the transparent substrate and the coupler means is filled with the refractive index matching liquid. Therefore, with the first surface plasmon sensor in accordance with the present invention, the exchange of the sensor unit can be carried out more easily and the distance between the sensor unit and the coupler means can be more easily kept to be equal to the predetermined value than with the conventional surface plasmon sensor, in which a refractive index matching liquid is coated on the joint area between a sensor unit and a coupler, and in which the sensor unit and the coupler are thereby brought into close contact with each other.

With the second surface plasmon sensor in accordance with the present invention, the sensor unit, which is provided with the transparent substrate and the metal film located on one surface side of the transparent substrate and brought into contact with a sample, is supported by the sensor unit support means, such that the distance between the transparent substrate and the coupler means may be kept to be equal to a predetermined value. Also, the space between the transparent substrate and the coupler means is filled with the refractive index matching liquid. Further, the second surface plasmon sensor in accordance with the present invention is provided with either one or both of the incidence position shifting means and the sensor unit relative movement means. The incidence position shifting means shifts the incidence position of the light beam at the light beam entry portion such that the light beam may successively impinge upon different portions of the interface, which are taken along a predetermined direction. The sensor unit relative movement means moves the sensor unit with respect to the coupler means and along a predetermined direction such that the aforesaid distance may be kept to be equal to the predetermined value. Therefore, with the second surface plasmon sensor in accordance with the present invention, one- or two-dimensional scanning can be carried out.

In particular, with the second surface plasmon sensor in accordance with the present invention, wherein the space between the transparent substrate and the coupler means is constituted of the layer of the refractive index matching liquid, the movement of the sensor unit with respect to the coupler means can be carried out easily.

Also, the second surface plasmon sensor in accordance with the present invention may comprise both of the incidence position shifting means and the sensor unit relative movement means, and the predetermined direction, along which the different portions of the interface are taken in the shifting operation carried out by the incidence position shifting means, and the predetermined direction, along which the sensor unit is moved with respect to the coupler means by the sensor unit relative movement means, may intersect with each other. In such cases, two-dimensional scanning can be carried out over a wide area.

With the second surface plasmon sensor in accordance with the present invention, wherein a two-dimensional analysis can be carried out, two-dimensional information representing physical properties of a sample can be obtained, and analyses of a plurality of samples can be carried out efficiently.

With the third surface plasmon sensor in accordance with the present invention, wherein the hologram optical element is employed for the coupling of the light beam with the sensor section, multiple reflection interference, which will occur when a prism is employed, can be prevented from occurring. Also, the surface plasmon sensor can be kept smaller in size and adjustments of an optical axis can be carried out more easily than when a prism is employed.

The third surface plasmon sensor in accordance with the present invention may be constituted such that the hologram optical element may be designed to converge the incident collimated light beam to a predetermined position, and the light source moving means may be provided, the light source moving means moving the light source in a plane, which is parallel to the interface, and in a direction heading towards the predetermined position or in a direction heading away from the predetermined position. In such cases, various different angles of incidence upon the interface can be obtained at a predetermined position.

Also, with the third surface plasmon sensor in accordance with the present invention, wherein the hologram optical element has the lens functions and the aberration compensating functions or has the cylindrical lens functions and the aberration compensating functions, the light beam can be converged to the predetermined position such that no aberration may occur on the interface.

Further, with the third surface plasmon sensor in accordance with the present invention, which is provided either one or both of the sensor unit moving means and the incidence position shifting means, an analysis of a sample, which extends in a one-dimensional direction or in two-dimensional directions, and analyses of a plurality of samples, which are arrayed in a one-dimensional direction or in two-dimensional directions, can be carried out efficiently.

BRIEF DESCRIPTION OF THE DRAWINGS

FIG. 1 is a side view showing a first embodiment of the surface plasmon sensor in accordance with the present invention, FIG. 2 is a graph showing approximate relationship between an angle of incidence of a light beam upon a reflection interface and an intensity of a reflected light, which is detected by a photo detecting means, in a surface plasmon sensor, FIG. 7 is a side view showing a sixth embodiment of the surface plasmon sensor in accordance with the present invention, FIG. 8 is a side view showing a seventh embodiment of the surface plasmon sensor in accordance with the present invention, FIG. 13 is a side view showing an eighth embodiment of the surface plasmon sensor in accordance with the present invention, FIG. 14 is a view taken from a direction indicated by the arrow A in FIG. 13, FIG. 15 is a view taken from a direction indicated by the arrow B in FIG. 13, FIG. 16 is a side view showing a ninth embodiment of the surface plasmon sensor in accordance with the present invention, FIG. 17 is a side view showing a tenth embodiment of the surface plasmon sensor in accordance with the present invention, FIG. 19 is a view taken from a direction indicated by the arrow A in FIG. 18, FIG. 20 is a view taken from a direction indicated by the arrow B in FIG. 18, FIG. 25 is a view taken from a direction indicated by the arrow A in FIG. 24.

DESCRIPTION OF THE PREFERRED EMBODIMENTS

Figure 3:
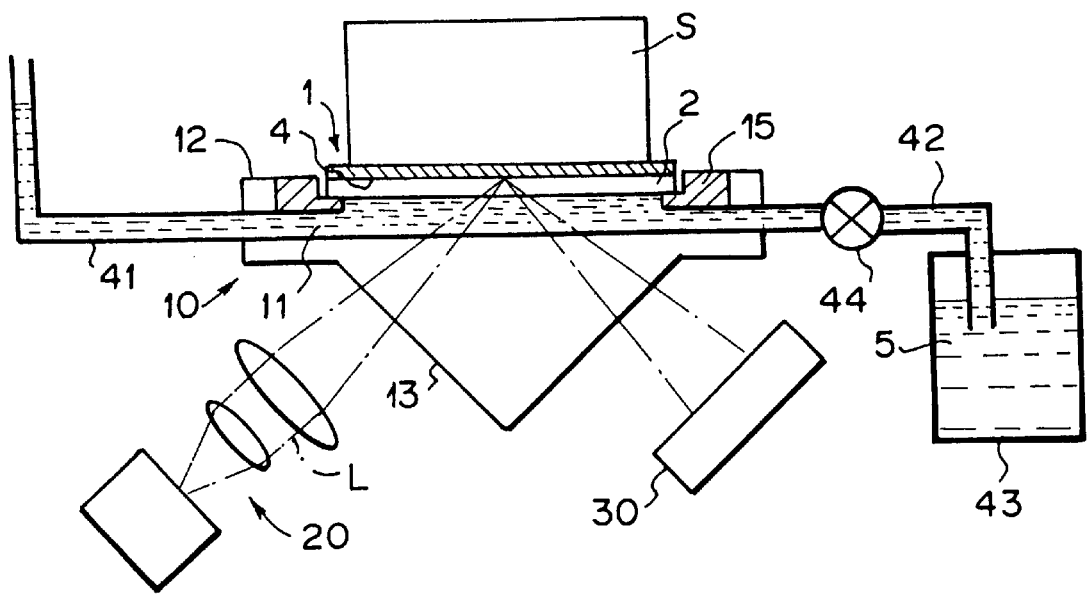
FIG. 3 is a side view showing a second embodiment of the surface plasmon sensor in accordance with the present invention.

The present invention will hereinbelow be described in further detail with reference to the accompanying drawings.

FIG. 1 is a side view showing a first embodiment of the surface plasmon sensor in accordance with the present invention.

As illustrated in FIG. 1, basically, the surface plasmon sensor comprises a sensor unit 1 provided with a metal film, which is brought into contact with a sample S to be analyzed and may be constituted of gold, silver, or the like. The surface plasmon sensor also comprises a sensor unit support means 15 for supporting the sensor unit 1. The surface plasmon sensor further comprises a coupler means 10, which is located with respect to the sensor unit 1. A refractive index matching liquid (hereinbelow referred to simply as the matching liquid) 5 intervenes between the sensor unit 1 and the coupler means 10. The surface plasmon sensor still further comprises a light-source optical means 20 for producing a light beam and causing the light beam to enter into the coupler means 10, and a photo detecting means 30 for detecting the ATR angle $\theta_{sp}$ from the light beam having been radiated out of the coupler means 10.

The first embodiment of the surface plasmon sensor in accordance with the present invention will hereinbelow be described in more detail.

The sensor unit 1 comprises a transparent substrate (a sensor substrate) 2, which may be constituted of glass, or the like, and a metal film 3, which is formed on the transparent substrate 2 and may be constituted of gold, silver, or the like. When the metal film 3, which may be constituted of gold, or the like, is formed on the transparent substrate 2, a chromium layer having a thickness of approximately 1 nm is firstly overlaid on the transparent substrate 2 and thereafter the metal film 3 is formed on the chromium layer. With such a technique, the formation of the metal film 3 can be carried out easily, and peeling of the metal film 3 can be restricted. Also, in analyses with the surface plasmon sensor, ordinarily, a bonding reaction film, to which an antigen (or an antibody) has been fixed, is formed on the metal film 3, and an antigen-antibody reaction responding selectively to a specific substance is utilized. In this manner, the amount of an antibody (or an antigen), which is specifically adsorbed by the bonding reaction film, is determined from a change in angle of incidence of the light beam.

The coupler means 10 comprises a cell 12, which is constituted of glass and has a recess 11 on the side facing the sensor unit 1, and a prism 13, which is formed on the other side of the cell 12. The sensor unit support means (hereinbelow referred to as the sensor unit attachment) 15 for supporting the sensor unit 1 is located at a portion of the coupler means 10. The sensor unit attachment 15 supports the sensor unit 1 such that the distance between the transparent substrate 2 and the cell 12 may be equal to a predetermined value. The space between the transparent substrate 2 and the coupler means 10 is filled with the matching liquid 5. The transparent substrate 2, the coupler means 10, and the matching liquid 5 have refractive indexes approximately equal to one another.

The light-source optical means 20 comprises a light source 21, which produces a light beam L and may be constituted of a semiconductor laser, or the like. The light-source optical means 20 also comprises a collimator lens 22 and a converging lens 23, which receive the light beam L and cause it to enter into the prism 13 from its one surface. The light beam L, which has been produced by the light source 21, is converted by a polarizer (not shown) into P-polarized light and is then caused to enter into the prism 13. The converged light beam L contains components, which impinge at various different angles of incidence θ upon an interface 4 between the transparent substrate 2 and the metal film 3. The angles of incidence θ are set to be not smaller than the total reflection critical angle, such that the light beam L may be totally reflected from the interface 4.

Alternatively, the light-source optical means may be constituted of a light source for producing a single light beam having a small beam diameter, and a goniometer for rotating the light source. The light source may be rotated by the goniometer, and the angle of incidence θ of the light beam may thereby be set to be various different angles. As another alternative, instead of the goniometer being used, the light beam may be deflected by a galvanometer mirror, and various different angles of incidence may thereby be obtained. (Such a technique is proposed in Japanese Unexamined Patent Publn. No. 9(1997)-292335.)

In accordance with a change in angle of incidence, the angle of reflection of the light beam L, which is reflected from the interface 4, changes. Therefore, as the photo detecting means 30, means having light receiving elements arrayed in the direction along which the angle of reflection changes, such as a CCD line sensor, may be employed. Alternatively, a photodiode, a two-part photodiode proposed in U.S. Ser. No. 08/840,648, a photodiode array, or the like, may be employed.

How a sample analysis is carried out in the surface plasmon sensor having the constitution described above will be described hereinbelow. The sample S to be analyzed is located such that it may be in contact with the metal film 3. The light beam L, which has been produced and converted into the P-polarized light by the light-source optical means 20, enters into the prism 13 from its one surface. The light beam L passes through the prism 13 and impinges upon the interface 4. As described above, the light beam L, which has been converged and irradiated, impinges at various angles of incidence θ upon the interface 4 between the metal film 3 and the transparent substrate 2. The light beam L is then totally reflected from the interface 4, again passes through the prism 13, and is then radiated out of the other surface of the prism 13. The intensity of the light beam L, which has thus been radiated out of the prism 13, is detected by the photo detecting means 30.

A photo detection signal, which is detected by each of the light receiving elements of the photo detecting means 30, represents the intensity I of the totally reflected light beam L with respect to each of the angles of incidence θ upon the interface 4. FIG. 2 approximately shows the relationship between the intensity I of the reflected light beam and the angles of incidence θ.

The light impinging at a specific angle of incidence (i.e., the ATR angle) $\theta_{sp}$ upon the interface 4 excites surface plasmon at an interface between the metal film 3 and the sample S. As for the light impinging at the specific angle of incidence $\theta_{sp}$ upon the interface 4, the intensity I of the reflected light becomes markedly low. From the photo detection signal detected by each of the light receiving elements of the photo detecting means 30, the ATR angle $\theta_{sp}$ can be determined. As described above in detail, the specific substance contained in the sample S can be analyzed quantitatively in accordance with the value of the ATR angle $\theta_{sp}$.

A second embodiment of the surface plasmon sensor in accordance with the present invention will be described hereinbelow with reference to FIG. 3. In the second embodiment (and third to sixth embodiments described later), as for the same constitutions and the same operating sections as those in the aforesaid first embodiment, detailed explanation will be omitted.

In the second embodiment, pipes 41 and 42, which allow the matching liquid 5 to flow into and out of the space between the sensor unit 1 and the coupler means 10, are located such that one end of each pipe may be inserted through the wall of the cell 12. The pipe 41 has an opening at the other end, which is located at a position higher than the bottom surface of the transparent substrate 2 with respect to the vertical direction. The pipe 41 thereby forms a vacant member, which allows the matching liquid 5 to be introduced up to a position higher than the bottom surface of the transparent substrate 2. The other end of the pipe 42 is inserted into a matching liquid tank 43, which stores the matching liquid 5. A pump 44 is located at an intermediate position between the two ends of the pipe 42. The pipe 42, the matching liquid tank 43, and the pump 44 together constitute the matching liquid supply means.

In the second embodiment of the surface plasmon sensor in accordance with the present invention, the sensor unit 1 is supported by the sensor unit attachment 15, and thereafter the pump 44 is operated to supply the matching liquid 5 from the matching liquid tank 43, through the pipe 42, and into the space between the transparent substrate 2 and the coupler means 10. The matching liquid 5 is supplied until the level of the matching liquid 5, which has entered into the pipe 41, becomes higher than the bottom surface of the transparent substrate 2. In this manner, the space between the transparent substrate 2 and the coupler means 10 can be completely filled with the matching liquid 5.

Figure 4:
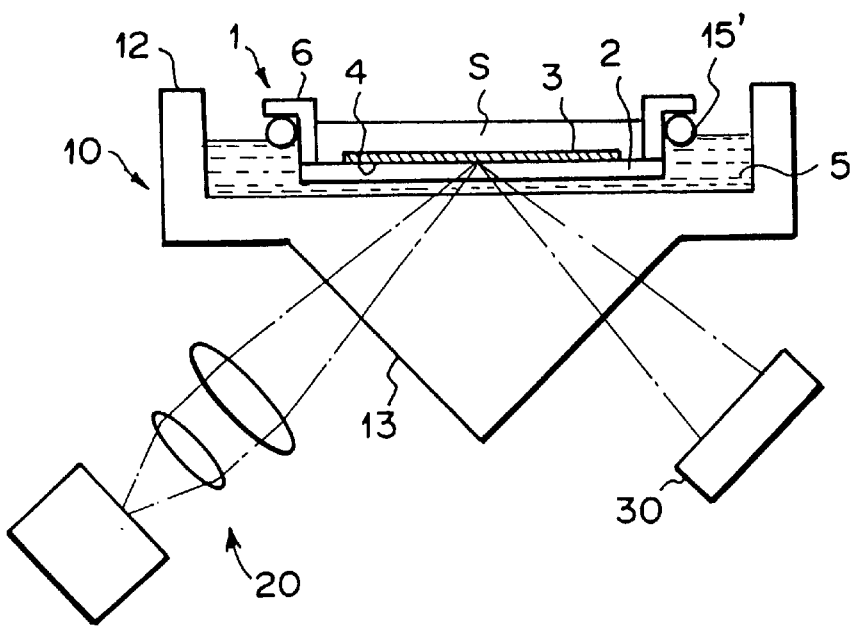
FIG. 4 is a side view showing a third embodiment of the surface plasmon sensor in accordance with the present invention.

A third embodiment of the surface plasmon sensor in accordance with the present invention will be described hereinbelow with reference to FIG. 4. In the third embodiment, the sensor unit 1 comprises the transparent substrate 2 and the metal film 3 formed on the transparent substrate 2, and a waterproof wall 6 is formed so as to surround the metal film 3.

Also, a sensor unit attachment 15' is associated with the coupler means 10. The sensor unit attachment 15' supports a portion of the waterproof wall 6 and thereby supports the sensor unit 1, such that the transparent substrate 2 of the sensor unit 1 may be immersed in the matching liquid 5. The sensor unit attachment 15' thus determines the position of the sensor unit 1 with respect to the position of the coupler means 10.

Figure 5:
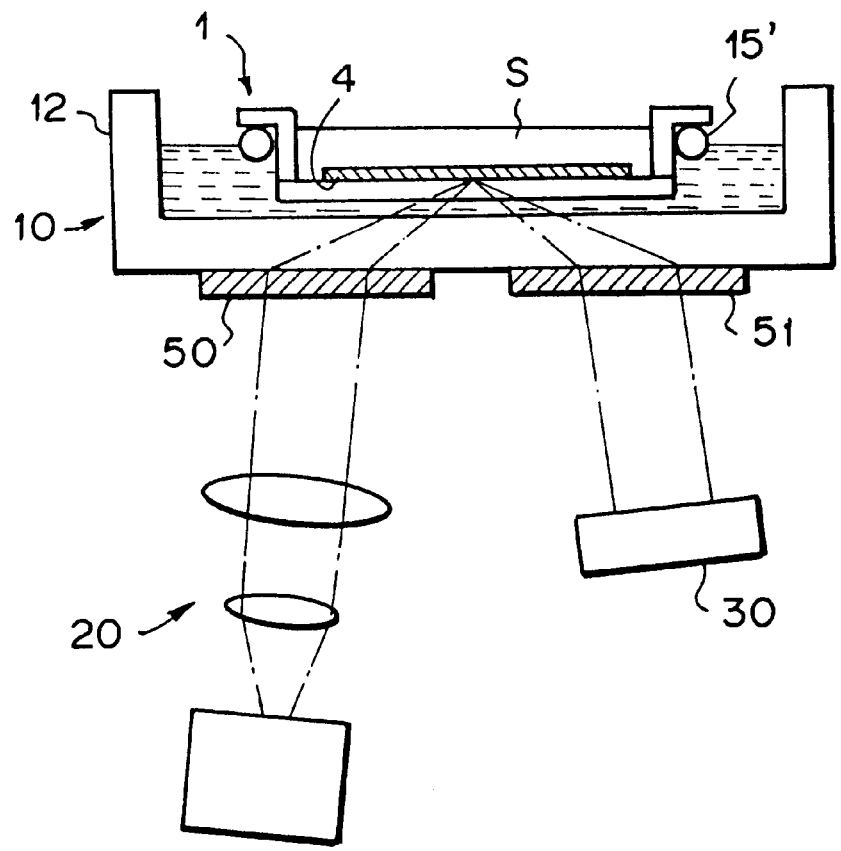
FIG. 5 is a side view showing a fourth embodiment of the surface plasmon sensor in accordance with the present invention.

In the first, second, and third embodiments described above, the coupler means 10 is provided with the prism 13. However, in the surface plasmon sensor in accordance with the present invention, the coupler means need not necessarily be provided with the prism. For example, as in a fourth embodiment shown in FIG. 5, diffraction gratings 50 and 51 may be formed on the cell 12, and the light beam L may be entered from the diffraction grating 50 and radiated out of the diffraction grating 51. In such cases, the light beam L is diffracted by the diffraction grating 50 for the entry of the light beam and is caused to impinge upon the interface 4 at an angle of incidence θ. The light beam L is then totally reflected from the interface 4, diffracted by the diffraction grating 51 for radiation of the light beam, and radiated out of the coupler means 10. The intensity of the light beam L, which has thus been radiated out of the coupler means 10, is detected by the photo detecting means 30.

Figure 6:
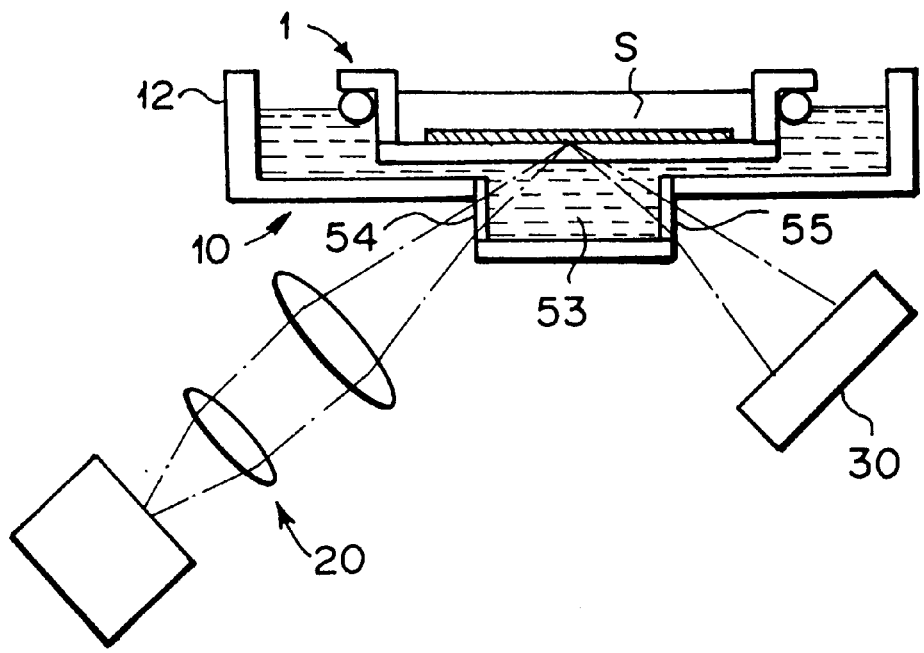
FIG. 6 is a side view showing a fifth embodiment of the surface plasmon sensor in accordance with the present invention.

Alternatively, as in a fifth embodiment shown in FIG. 6, a portion 53, which is convex downwardly, may be formed at the bottom surface of the cell 12, and the matching liquid 5 may be filled in the region inside of the convex portion 53. The lateral faces of the convex portion 53 may be constituted of glass windows 54 and 55, and the light beam L may be entered from the glass window 54 and radiated out of the glass window 55. The glass windows 54 and 55 are constituted of a material having a refractive index approximately equal to the refractive indexes of the transparent substrate 2 and the matching liquid 5. In such cases, portions of the cell 12 other than the glass windows 54 and 55 need not be permeable to light.

A sixth embodiment of the surface plasmon sensor in accordance with the present invention will be described hereinbelow with reference to FIG. 7. In this embodiment, the sensor unit 1 comprises a sensor section 104 and a sensor section holding member 105 for holding the sensor section 104. The sensor section 104 is constituted of a main transparent substrate 102 and a metal film 103 located on the main transparent substrate 102. The bottom surface of the sensor section holding member 105 is constituted of a supporting transparent substrate 106, which has a refractive index approximately equal to the refractive index of the main transparent substrate 102 of the sensor section 104. An analysis is carried out while the main transparent substrate 102 of the sensor section 104 is being in close contact with the supporting transparent substrate 106 via the matching liquid. As in the embodiments described above, the bonding reaction film is formed on the metal film 103. At the time of sensor exchange, the sensor unit 1 may be exchanged with a new one. Alternatively, only the sensor section 104 may be exchanged with a new one. Since the sensor section 104 has the simple constitution, its cost can be kept low, and it can be exchanged easily. Also, as the sensor section 104, one of sensor sections having different sizes or different forms can be used.

In the sixth embodiment of FIG. 7, as in the fifth embodiment of FIG. 6, the coupler means 10 is constituted such that a portion 113, which is convex downwardly, may be formed at a portion of a cell 112, and the lateral faces of the convex portion 113 may be constituted of glass windows 114 and 115. The light beam L is entered from the glass window 114 and radiated out of the glass window 115. At the time of an analysis, the matching liquid 5 is filled in the recess, which is surrounded by the cell 112 and an optical system case housing 141 described later, such that the bottom surface of the sensor section holding member 105 may be immersed in the matching liquid 5.

The light-source optical means 20, which produces the light beam L and causes it to enter into the coupler means 10, comprises a light source device 123, which is provided with a light source 121, such as a semiconductor laser, and a collimator lens 122. The light-source optical means 20 also comprises a mirror 64 for reflecting the light beam L having been radiated out of the light source device 123, and a converging lens 65. The light beam L, which has been radiated out of the light source device 123, is converted by a polarizer (not shown) into P-polarized light and is then caused to enter into the coupler means 10. The converged light beam L contains components, which impinge at various different angles of incidence θ upon an interface 107 between the main transparent substrate 102 and the metal film 103. The angles of incidence θ are set to be not smaller than the total reflection critical angle, such that the light beam L may be totally reflected from the interface 107.

The photo detecting means 30 detects the light beam, which has been reflected from the interface 107 and has then been radiated out of the glass window 115 of the coupler means 10. A converging lens 66 is located on the side of the photo detecting means 30, such that the light beam may be reliably detected by the photo detecting means 30.

In the sixth embodiment of FIG. 7, the coupler means 10, the light-source optical means 20, and the photo detecting means 30 are located on a base 140. On the base 140, the optical system case housing 141 is formed such that it may surround the light-source optical means 20, and the like. The coupler means 10 is secured to the optical system case housing 141. Also, the converging lens 65 on the side of the light-source optical means 20 and the converging lens 66 on the side of the photo detecting means 30 are hung from and supported by the lower surface of the coupler means 10.

A case housing 142 is formed on the base 140 such that the case housing 142 may surround the optical system case housing 141. A sensor unit attachment 143 for supporting the sensor unit 1 is secured to the top surface of the case housing 142. The sensor unit 1 is secured to the sensor unit attachment 143, which is secured to the case housing 142. The sensor unit 1 is thus supported such that the distance between the sensor unit 1 and the coupler means 10 may be kept to be equal to the predetermined value.

In the embodiments described above, the ATR angle $\theta_{sp}$ is obtained from the intensity of the reflected light with respect to various different angles of incidence. Alternatively, the ATR angle $\theta_{sp}$ may be obtained by utilizing the characteristics such that the intensity of the reflected light with respect to a certain angle of incidence changes in accordance with the value of the ATR angle $\theta_{sp}$. For example, the angle of incidence of the light beam may be set at a predetermined angle smaller than the ATR angle $\theta_{sp}$, and the ATR angle $\theta_{sp}$ may be obtained in accordance with the intensity of the reflected light, which is obtained at this time.

Seventh to thirteenth embodiments of the surface plasmon sensor in accordance with the present invention will be described hereinbelow.

Figure 9:
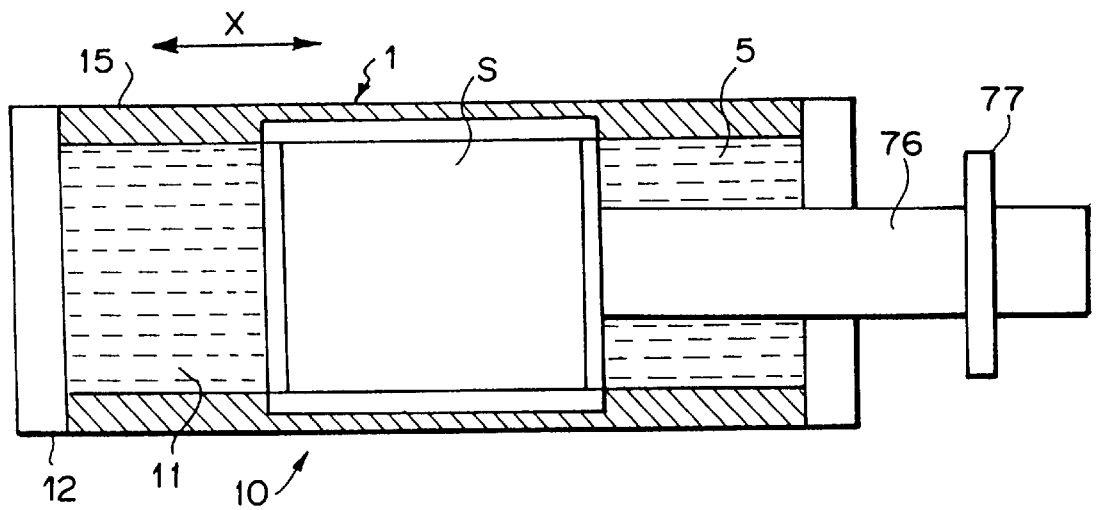
FIG. 9 is a view taken from a direction indicated by the arrow A in FIG. 8.
Figure 10:
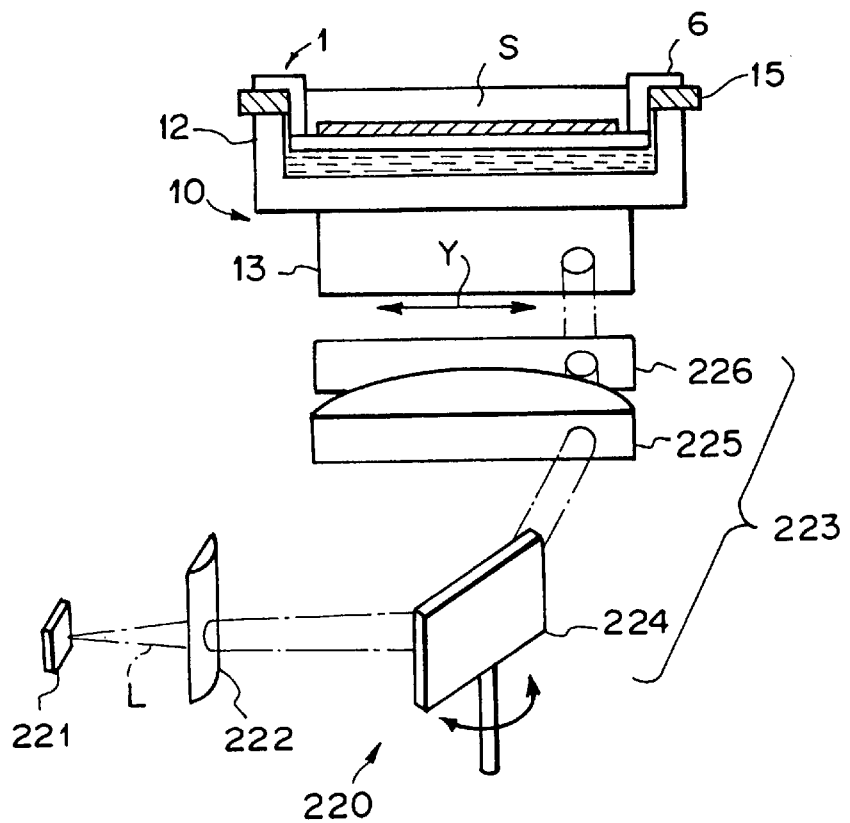
FIG. 10 is a view taken from a direction indicated by the arrow B in FIG. 8.

FIG. 8 is a side view showing a seventh embodiment of the surface plasmon sensor in accordance with the present invention. FIG. 9 is a view taken from a direction indicated by the arrow A in FIG. 8. FIG. 10 is a view taken from a direction indicated by the arrow B in FIG. 8. FIG. 10 is a fragmentally sectional view.

As illustrated in FIG. 8, basically, the surface plasmon sensor comprises the sensor unit 1 provided with the metal film, which is brought into contact with the sample S to be analyzed and may be constituted of gold, silver, or the like. The surface plasmon sensor also comprises the sensor unit support means 15 for supporting the sensor unit 1. The surface plasmon sensor further comprises the coupler means 10, which is located with respect to the sensor unit 1. The matching liquid 5 intervenes between the sensor unit 1 and the coupler means 10. The surface plasmon sensor still further comprises a light-source optical means 220 for producing a light beam and causing the light beam to enter into the coupler means 10, and the photo detecting means 30 for detecting the ATR angle $\theta_{sp}$ from the light beam having been radiated out of the coupler means 10.

The seventh embodiment of the surface plasmon sensor in accordance with the present invention will hereinbelow be described in more detail.

The sensor unit 1 comprises the transparent substrate (the sensor substrate) 2, which has uniform thickness and may be constituted of glass, or the like, and the metal film 3, which is formed on the transparent substrate 2 and may be constituted of gold, silver, or the like. The waterproof wall 6 is formed such that it may surround the metal film 3. In this embodiment, the combination of the metal film 3 and the bonding reaction film, which is formed on the metal film 3, is referred to as the sensor film. The surface plasmon sensor provided with the sensor unit 1 having the constitution described above has the advantages described below over the conventional surface plasmon sensor, in which a matching liquid is coated on the joint area between a substrate of a sensor unit and a coupler means, and in which the substrate and the coupler means are thereby directly brought into close contact with each other. Specifically, at the time of sensor exchange, or the like, the distance between the sensor unit 1 and the coupler means 10 can be easily kept to be equal to the predetermined value, and fine adjustments of the thickness of the matching liquid coat, and the like, need not be carried out. Therefore, the sensor exchange can be carried out easily. Also, the sensor exchange can be carried out automatically.

The coupler means 10 comprises the cell 12, which is constituted of glass and has the recess 11 on the side facing the sensor unit 1, and the prism 13, which has a triangular prism shape and is formed on the other side of the cell 12. The sensor unit support means (the sensor unit attachment) 15 for supporting the sensor unit 1 is located at a portion of the coupler means 10. The sensor unit attachment 15 supports the sensor unit 1 such that the distance between the transparent substrate 2 and the cell 12 may be equal to the predetermined value. Specifically, in this embodiment, the sensor unit attachment 15 supports a portion of the waterproof wall 6 and thereby supports the sensor unit 1, such that the transparent substrate 2 of the sensor unit 1 may be immersed in the matching liquid 5. The sensor unit attachment 15 thus determines the position of the sensor unit 1 with respect to the position of the coupler means 10. The space between the transparent substrate 2 and the coupler means 10 is filled with the matching liquid 5. The transparent substrate 2, the coupler means 10, and the matching liquid 5 have refractive indexes approximately equal to one another.

As illustrated in FIG. 9, the coupler means 10 has a structure extending in one direction, and the sensor unit attachment 15 is formed along the recess 11. The sensor unit attachment 15 is provided with a conveying rail (not shown), and the sensor unit 1 can be moved along the conveying rail. A conveying shaft 76 is secured to the sensor unit 1. Also, the conveying shaft 76 is grasped between rollers 77, 77 and moved by the rotation of the rollers 77, 77. In accordance with the rotation of the rollers 77, 77, the conveying shaft 76 is moved, and the sensor unit 1 is moved by the conveying shaft 76 in the directions indicated by the double headed arrow X. Specifically, in the seventh embodiment, the sensor unit relative movement means is constituted by the conveying rail of the sensor unit attachment 15, the conveying shaft 76, and the rollers 77, 77.

The light-source optical means 220 comprises a light source 221, which produces a light beam L and may be constituted of a semiconductor laser, or the like. The light-source optical means 220 also comprises a cylindrical lens 222 and a telecentric scanner 223, which is a light deflecting means utilizing a telecentric optical system. The telecentric scanner 223 comprises a galvanometer mirror 224, which is located at the position corresponding to the focal length of the cylindrical lens 222, and two cylindrical lenses 225 and 226. The light beam L, which has been produced by the light source 221, is focalized on the galvanometer mirror 224 by the cylindrical lens 222. The light beam L is then reflected from the galvanometer mirror 224 and impinges upon the cylindrical lens 225 of the telecentric scanner 223. The light beam L is collimated by the cylindrical lens 225 and caused by the cylindrical lens 226 to enter into the prism 13. At this time, by the cylindrical lens 226, the light beam L is converged in the plane, which is normal to the major axis of the prism 13, and on the interface 4 between the metal film 3 and the transparent substrate 2. In accordance with the swinging operation of the galvanometer mirror 224, the position of incidence of the light beam L upon the prism 13 is shifted in parallel along the directions indicated by the double headed arrow Y. The light beam L, which has been produced by the light source 221, is caused to enter into the prism 13 as P-polarized light. The converged light beam L contains components, which impinge at various different angles of incidence θ upon the interface 4 between the transparent substrate 2 and the metal film 3. The angles of incidence θ are set to be not smaller than the total reflection critical angle, such that the light beam L may be totally reflected from the interface 4.

In the seventh embodiment of FIG. 8, as described above, the telecentric scanner 223, which is the light deflecting means, is employed as the means for shifting the incidence position of the light beam L. Alternatively, as the incidence position shifting means, for example, a light source moving means may be employed. Specifically, the light source may be located on a stage, which can be mechanically moved in the directions indicated by the double headed arrow Y. Also, the light source moving means may move the stage and thereby move the light source itself, such that the incidence position of the light beam may be shifted in parallel along the directions indicated by the double headed arrow Y.

In accordance with a change in angle of incidence of the light beam L upon the interface 4, the angle of reflection of the light beam L, which is reflected from the interface 4, changes. Therefore, as the photo detecting means 30, means having light receiving elements arrayed in the direction along which the angle of reflection changes, such as a CCD line sensor, may be employed. Alternatively, a photodiode, a two-part photodiode proposed in U.S. Ser. No. 08/840,648, a photodiode array, or the like, may be employed. However, the location of the photo detecting means 30 is regulated such that it can reliably detect the totally reflected light beam, which comes from the radiating position changing in accordance with the change in the position of incidence of the light beam L upon the prism 13.

Figure 11A:
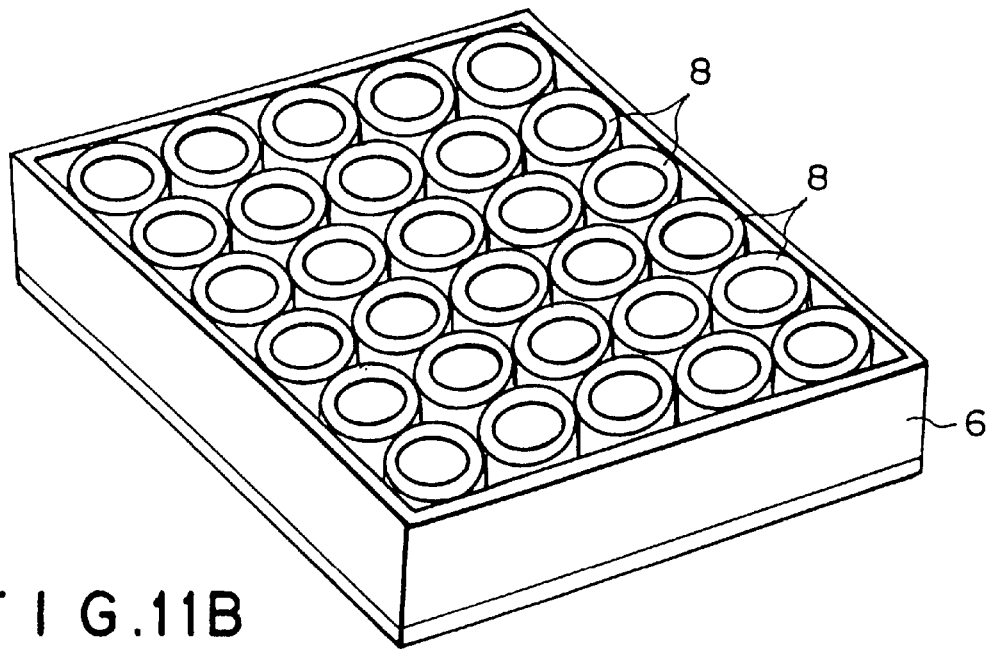
FIG. 11A is a perspective view showing a multi-channel type of sensor.
Figure 11B:
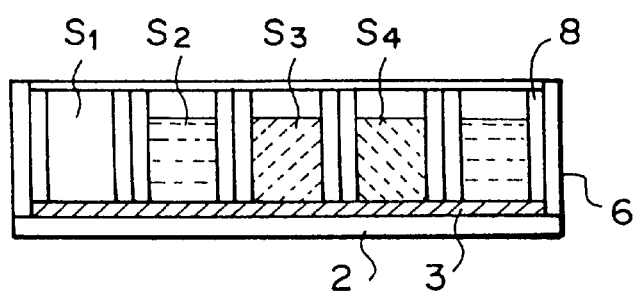
FIG. 11B is a sectional view showing the multi-channel type of sensor shown in FIG. 11A.

How the sample analyses are carried out in the seventh embodiment of the surface plasmon sensor having the constitution described above will be described hereinbelow. Firstly, as illustrated in FIG. 11A, a plurality of sample cells 8, 8, . . . are located on the sensor film, and different samples Sn ($S_1$, $S_2$, $S_3$, . . . ) are introduced into the sample cells 8, 8, . . . The samples Sn are thus located such that they may be in contact with the sensor film. FIG. 11B is a sectional view of FIG. 11A.

Thereafter, an analysis is carried out on each of the samples. In the sample analysis, for each sample, the light beam L, which has been set as the P-polarized light, is entered into the prism 13 from its one surface. The light beam L passes through the prism 13 and impinges upon the interface 4. As described above, the light beam L, which has been converged and irradiated, impinges at various angles of incidence θ upon the interface 4 between the metal film 3 and the transparent substrate 2. The light beam L is then totally reflected from the interface 4, again passes through the prism 13, and is then radiated out of the other surface of the prism 13. The intensity of the light beam L, which has thus been radiated out of the prism 13, is detected by the photo detecting means 30. At this time, the photo detection signal, which is detected by the photo detecting means 30, represents the intensity I of the totally reflected light beam L with respect to each of the angles of incidence θ upon the interface 4. FIG. 2 approximately shows the relationship between the intensity I of the reflected light beam and the angles of incidence θ.

The light impinging at a specific angle of incidence (i.e., the ATR angle) $\theta_{sp}$ upon the interface 4 excites surface plasmon at the interface between the metal film 3 and the sample Sn. As for the light impinging at the specific angle of incidence $\theta_{sp}$ upon the interface 4, the intensity I of the reflected light becomes markedly low. From the photo detection signal detected by each of the light receiving elements of the photo detecting means 30, the ATR angle $\theta_{sp}$ can be determined. As described above in detail, a specific substance contained in the sample Sn can be analyzed quantitatively in accordance with the value of the ATR angle $\theta_{sp}$.

In the seventh embodiment, the analysis is carried out on each of the plurality of samples Sn. For this purpose, the sensor unit 1 is intermittently conveyed along the conveying rail of the sensor unit attachment 15 and in the directions indicated by the double headed arrow X. Also, the light beam L is shifted in parallel by the telecentric scanner 223 and caused to impinge successively upon the portions of the interface 4, which correspond to the samples Sn. The two-dimensional scanning is thus carried out such that the light beam L may be irradiated under the same conditions with respect to the samples Sn. In this manner, the analyses of the plurality of the samples Sn can be carried out quickly and efficiently.

As described above, in the seventh embodiment, the two-dimensional scanning with the light beam L can be carried out. Therefore, the seventh embodiment is also applicable when, for example, a sample, such as a gel sheet having been used in electrophoresis, is located on the metal film 3 and scanned in two-dimensional directions, and two-dimensional information representing the physical properties of a substance, which is to be analyzed and is distributed in the sample, is thereby obtained.

Figure 12:
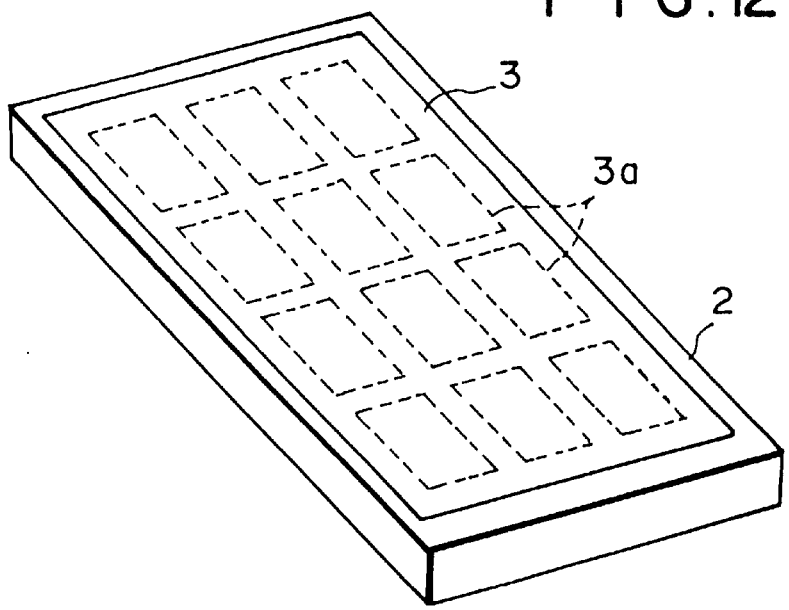
FIG. 12 is a perspective view showing a sensor film, which is divided into a plurality of regions.

Also, as illustrated in FIG. 12, a plurality of regions 3a, 3a, . . . may be set on the metal film 3, and sensor films provided with different bonding reaction films may be employed for the regions 3a, 3a, . . . In this condition, the two-dimensional scanning with the light beam may be carried out. In this manner, analyses of different immune reactions, and the like, which occur in the respective regions, can be carried out with respect to the respective regions.

An eighth embodiment of the surface plasmon sensor in accordance with the present invention will be described hereinbelow with reference to FIGS. 13, 14, and 15. FIG. 13 is a side view showing the eighth embodiment of the surface plasmon sensor in accordance with the present invention. FIG. 14 is a view taken from a direction indicated by the arrow A in FIG. 13. FIG. 15 is a view taken from a direction indicated by the arrow B in FIG. 13. In the eighth embodiment (and ninth to thirteenth embodiments described later), as for the same constitutions and the same operating sections as those in the aforesaid seventh embodiment, detailed explanation will be omitted.

In the eighth embodiment, the pipes 41 and 42, which allow the matching liquid 5 to flow into and out of the space between the sensor unit 1 and the coupler means 10, are located such that one end of each pipe may be inserted through the wall of the cell 12. The pipe 41 has an opening at the other end, which is located at a position higher than the bottom surface of the transparent substrate 2 with respect to the vertical direction. The pipe 41 thereby forms a vacant member, which allows the matching liquid 5 to be introduced up to a position higher than the bottom surface of the transparent substrate 2. The other end of the pipe 42 is inserted into the matching liquid tank 43, which stores the matching liquid 5. The pump 44 is located at an intermediate position between the two ends of the pipe 42. The pipe 42, the matching liquid tank 43, and the pump 44 together constitute the matching liquid supply means. The sensor unit 1 is not immersed in the matching liquid 5 as in the aforesaid seventh embodiment, and is located such that the bottom surface of the transparent substrate 2 may be in contact with the surface of the matching liquid 5.

In the eighth embodiment, conveying shafts 76', 76' are secured to the sensor unit 1 from its two sides. The conveying shafts 76', 76' have a large width, such that they may close the recess 11 of the cell 12, which is filled with the matching liquid 5. After the sensor unit 1 has been supported by the sensor unit attachment 15, the pump 44 is operated to supply the matching liquid 5 from the matching liquid tank 43, through the pipe 42, and into the space between the transparent substrate 2 and the coupler means 10. The matching liquid 5 is supplied until the level of the matching liquid 5, which has entered into the pipe 41, becomes higher than the bottom surface of the transparent substrate 2. In this manner, the space between the transparent substrate 2 and the coupler means 10 can be completely filled with the matching liquid 5.

One of the conveying shafts 76', 76' is grasped between rollers 77a', 77a', and the other conveying shaft 76' is grasped between rollers 77b', 77b. In accordance with the rotations of the rollers 77a', 77a' and the rollers 77b', 77b', the conveying shafts 76', 76' are moved, and the sensor unit 1 is moved by the conveying shafts 76', 76'.

In the seventh and eighth embodiments described above, the coupler means 10 is provided with the prism 13. However, in the surface plasmon sensor in accordance with the present invention, the coupler means need not necessarily be provided with the prism.

For example, as in a ninth embodiment shown in FIG. 16, the diffraction gratings 50 and 51 may be formed on the cell 12, and the light beam L may be entered from the diffraction grating 50 and radiated out of the diffraction grating 51. In such cases, the light beam L is diffracted by the diffraction grating 50 for the entry of the light beam and is caused to impinge upon the interface 4 at an angle of incidence θ. The light beam L is then totally reflected from the interface 4, diffracted by the diffraction grating 51 for radiation of the light beam, and radiated out of the coupler means 10. The intensity of the light beam L, which has thus been radiated out of the coupler means 10, is detected by the photo detecting means 30.

Alternatively, as in a tenth embodiment shown in FIG. 17, the portion 53, which is convex downwardly, may be formed at the bottom surface of the cell 12, and the matching liquid 5 may be filled in the region inside of the convex portion 53. The lateral faces of the convex portion 53 may be constituted of the glass windows 54 and 55, and the light beam L may be entered from the glass window 54 and radiated out of the glass window 55. The glass windows 54 and 55 are constituted of a material having a refractive index approximately equal to the refractive indexes of the transparent substrate 2 and the matching liquid 5. In such cases, portions of the cell 12 other than the glass windows 54 and 55 need not be permeable to light.

Figure 18:
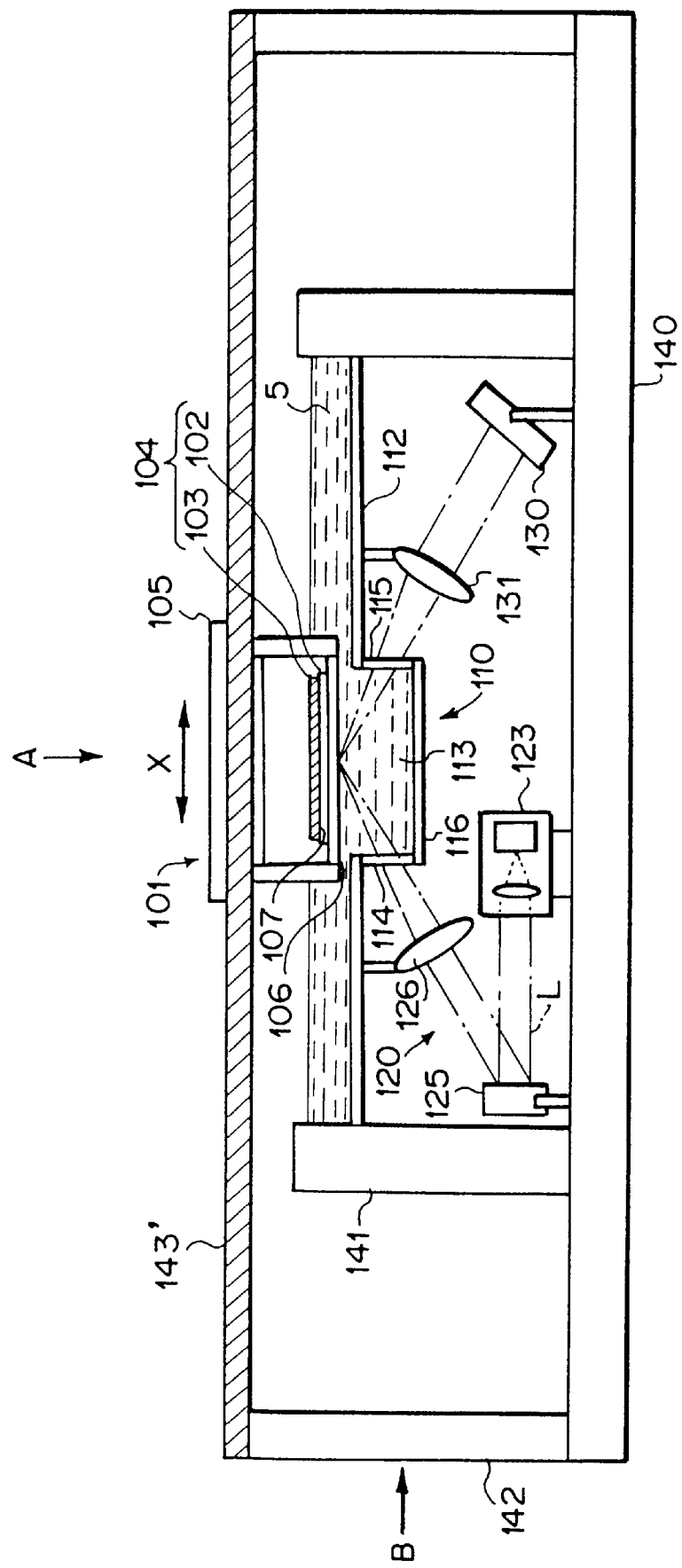
FIG. 18 is a side view showing an eleventh embodiment of the surface plasmon sensor in accordance with the present invention.

An eleventh embodiment of the surface plasmon sensor in accordance with the present invention will be described hereinbelow with reference to FIGS. 18, 19, and 20. FIG. 18 is a side view showing the eleventh embodiment of the surface plasmon sensor in accordance with the present invention. FIG. 19 is a view taken from a direction indicated by the arrow A in FIG. 18. FIG. 20 is a view taken from a direction indicated by the arrow B in FIG. 18. FIGS. 19 and 20 are fragmentally sectional views, in which several portions of the surface plasmon sensor are omitted.

In the eleventh embodiment, a sensor unit 101 comprises the sensor section 104 and the sensor section holding member 105 for holding the sensor section 104. The sensor section 104 is constituted of the main transparent substrate 102 and the metal film 103 located on the main transparent substrate 102. The bottom surface of the sensor section holding member 105 is constituted of the supporting transparent substrate 106, which has a refractive index approximately equal to the refractive index of the main transparent substrate 102 of the sensor section 104. An analysis is carried out while the main transparent substrate 102 of the sensor section 104 is being in close contact with the supporting transparent substrate 106 via the matching liquid. As in the seventh to tenth embodiments described above, the bonding reaction film is formed on the metal film 103. At the time of sensor exchange, the sensor unit 101 may be exchanged with a new one. Alternatively, only the sensor section 104 may be exchanged with a new one. Since the sensor section 104 has the simple constitution, its cost can be kept low, and it can be exchanged easily. Also, as the sensor section 104, one of sensor sections having different sizes or different forms can be used.

Figure 21:
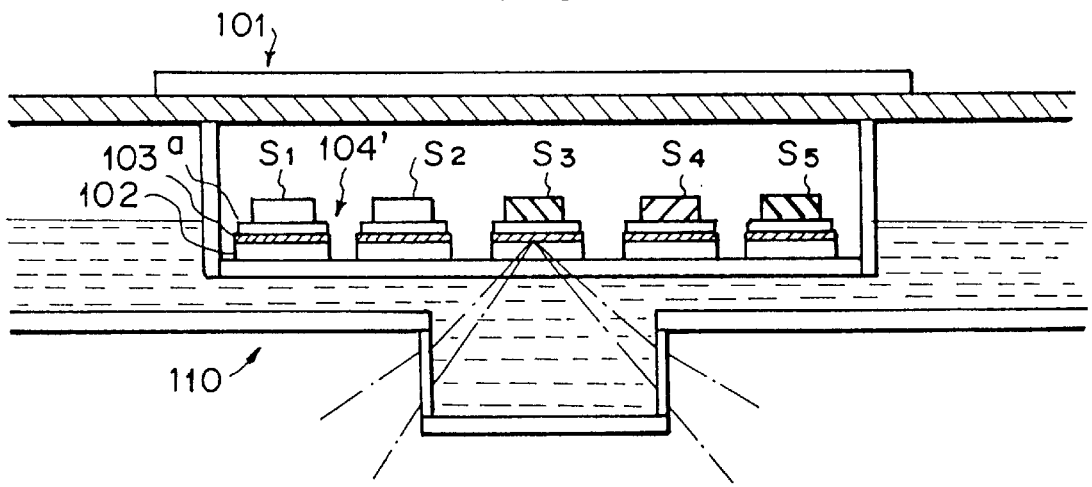
FIG. 21 is a side view showing a surface plasmon sensor provided with a plurality of sensor sections.
Figure 22:
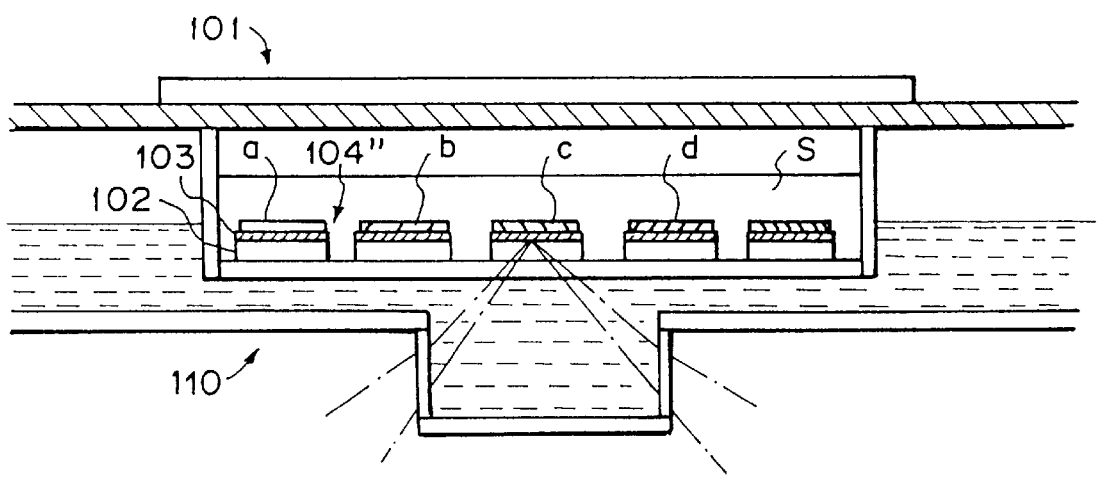
FIG. 22 is a side view showing a surface plasmon sensor provided with a plurality of sensor sections having different bonding reaction films.

As illustrated in FIG. 21, a plurality of sensor sections 104', 104', . . . having the same size or different sizes may be held by the sensor section holding member 105. The sensor sections 104', 104', . . . may be provided respectively with different samples Sn ($S_1, S_2, S_3, \ldots$), and analyses may be successively carried out with respect to the samples Sn. In such cases, bonding reaction films a, a, . . . are formed respectively on the metal films 103, 103, . . . of the sensor sections 104', 104', . . . Also, the samples Sn are located respectively on the respective bonding reaction films a, a, . . . Alternatively, as illustrated in FIG. 22, different kinds of bonding reaction films a, b, c, d, . . . containing different kinds of antigens (or antibodies) may be formed respectively on the metal films 103, 103, . . . of sensor sections 104", 104", . . . , and different phenomena occurring with a single sample S at the bonding reaction films a, b, c, d, . . . may be determined successively.

In the eleventh embodiment of FIG. 18, as in the tenth embodiment of FIG. 17, a coupler means 110 is constituted such that the portion 113, which is convex downwardly, may be formed at a portion of the cell 112, and the lateral faces of the convex portion 113 may be constituted of the glass windows 114 and 115. The light beam L is entered from the glass window 114 and radiated out of the glass window 115. At the time of an analysis, the matching liquid 5 is filled in the recess , which is surrounded by the cell 112 and the optical system case housing 141 described later, such that the bottom surface of the sensor section holding member 105 may be immersed in the matching liquid 5.

A light-source optical means 120 produces the light beam L and causes it to enter into the coupler means 110. The light-source optical means 120 comprises the light source device 123, which is provided with the light source 121, such as a semiconductor laser, and the collimator lens 122. The light-source optical means 120 also comprises a telecentric scanner 124, which is a light deflecting means utilizing a telecentric optical system. The telecentric scanner 124 comprises a galvanometer mirror 125 and an fθ lens 126. The light beam L is converged by the fθ lens 126 into a light spot and is caused to enter into the coupler means 110 from the glass window 114. In accordance with the swinging operation of the galvanometer mirror 125, the position of incidence of the light beam L upon the glass window 114 is shifted in parallel along the directions indicated by the double headed arrow Y. The light beam L, which has been radiated out of the light source device 123, is caused to enter into the coupler means 110 as P-polarized light. The converged light beam L contains components, which impinge at various different angles of incidence θ upon an interface 107 between the main transparent substrate 102 and the metal film 103. The angles of incidence θ are set to be not smaller than the total reflection critical angle, such that the light beam L may be totally reflected from the interface 107.

A detection means 130 detects the light beam, which has been reflected from the interface 107 and has then been radiated out of the glass window 115 of the coupler means 110. An fθ lens 131 is located on the side of the detection means 130, such that the light beam may be reliably detected by the detection means 130.

In the eleventh embodiment of FIG. 18, the coupler means 110, the light-source optical means 120, and the detection means 130 are located on the base 140. On the base 140, the optical system case housing 141 is formed such that it may surround the light-source optical means 120, and the like. The coupler means 110 is secured to the optical system case housing 141. Also, the fθ lens 126 on the side of the light-source optical means 120 and the fθ lens 131 on the side of the detection means 130 are hung from and supported by the lower surface of the coupler means 110.

The case housing 142 is formed on the base 140 such that the case housing 142 may surround the optical system case housing 141. A conveying rail 143', which extends along the directions indicated by the double headed arrow X and conveys the sensor unit 101, is located on the top surface of the case housing 142. The case housing 142 and the conveying rail 143', together constitute the sensor unit attachment for supporting the sensor unit 101 such that the distance between the sensor unit 101 and the coupler means 110 may be kept to be equal to the predetermined value. The sensor unit 101 can be moved along the conveying rail 143' in the directions indicated by the double headed arrow X, while the distance between the sensor unit 101 and the coupler means 110 is being kept to be equal to the predetermined value. Specifically, in the eleventh embodiment, the conveying rail 143', which is located on the base 140, corresponds to the sensor unit relative movement means.

As described above, in the eleventh embodiment, two-dimensional scanning can be carried out by the movement of the sensor unit 101 in the directions indicated by the double headed arrow X and the shifting of the light beam incidence position in the directions indicated by the double headed arrow Y, the shifting being conducted by the telecentric scanner 124 of the light-source optical means 120.

A twelfth embodiment of the surface plasmon sensor in accordance with the present invention will be described hereinbelow with reference to FIG. 23. In the twelfth embodiment, as in the eleventh embodiment of FIG. 18, the sensor unit 101, the coupler means 110, the light-source optical means 120, and the detection means 130 are employed. The light-source optical means 120 and the detection means 130 are located on a movable bed 145, and an optical system case housing 146 is formed on the movable bed 145 so as to surround the light-source optical means 120, and the like. The coupler means 110 is secured to the optical system case housing 146. Also, the fθ lens 126 on the side of the light-source optical means 120 and the fθ lens 131 on the side of the detection means 130 are hung from and supported by the lower surface of the coupler means 110.

A conveying rail 148, which extends in the direction indicated by the double headed arrow X, is located on a base 147. The movable bed 145 is located on the conveying rail 148 and can be moved along the conveying rail 148 in the direction indicated by the double headed arrow X. The movement of the movable bed 145 in the direction indicated by the double headed arrow X means that the light-source optical means 120 is moved in the direction indicated by the double headed arrow X. In accordance with the movement of the light-source optical means 120, the incidence position of the light beam L upon the interface 107 is shifted in the direction indicated by the double headed arrow X. On the base 147, a case housing 149 is formed such that it may surround the optical system case housing 146. The sensor unit 101 is secured to the top surface of the case housing 149. Specifically, the case housing 149 also serves as the sensor unit attachment for supporting the sensor unit 101. The sensor section 104 is provided with a sample supply unit 150 for supplying the sample S to be analyzed.

As described above, in the twelfth embodiment, two-dimensional scanning can be carried out by the movement of the movable bed 145 in the directions indicated by the double headed arrow X and the shifting of the light beam incidence position in the directions indicated by the double headed arrow Y, the shifting being conducted by the telecentric scanner 124 of the light-source optical means 120.

Figure 24:
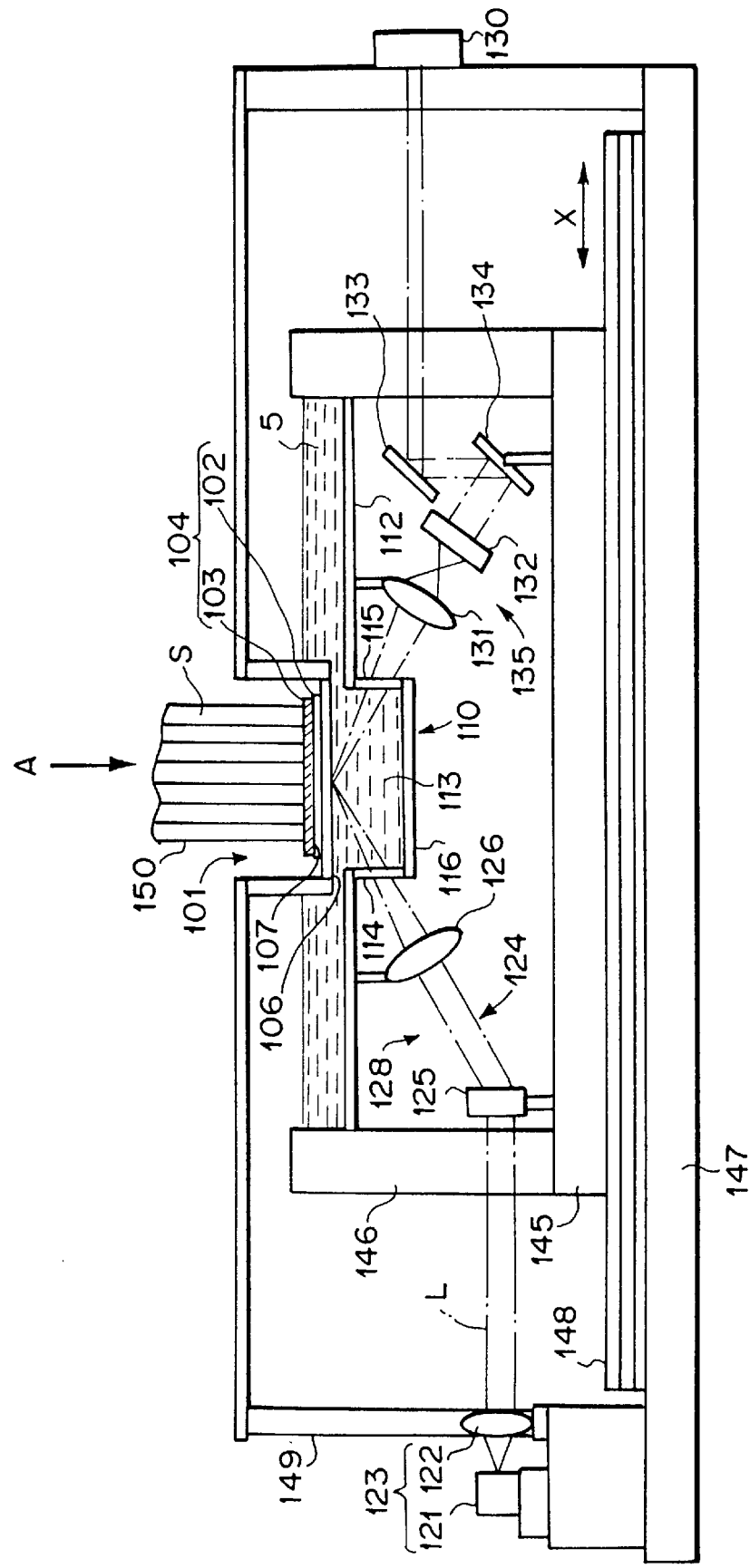
FIG. 24 is a side view showing a thirteenth embodiment of the surface plasmon sensor in accordance with the present invention.

A thirteenth embodiment of the surface plasmon sensor in accordance with the present invention will be described hereinbelow with reference to FIGS. 24 and 25. FIG. 24 is a side view showing the thirteenth embodiment of the surface plasmon sensor in accordance with the present invention. FIG. 25 is a view taken from a direction indicated by the arrow A in FIG. 24. FIG. 25 is a fragmentally sectional view, in which several portions of the surface plasmon sensor are omitted.

Figure 23:
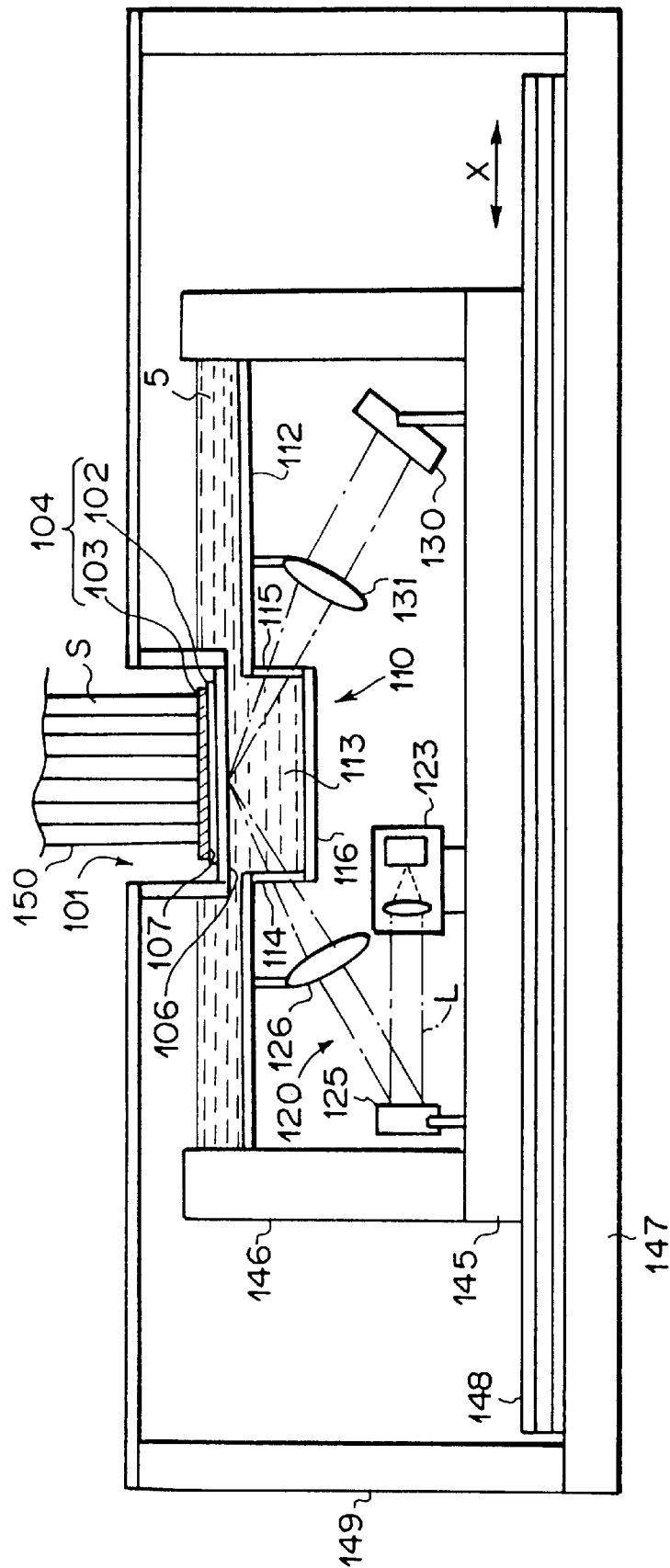
FIG. 23 is a side view showing a twelfth embodiment of the surface plasmon sensor in accordance with the present invention.

As in the twelfth embodiment of FIG. 23, the thirteenth embodiment of FIG. 24 is provided with the two-dimensional scanning mechanism. However, the thirteenth embodiment is different from the twelfth embodiment in that the light source device 123, which is provided with the light source 121, such as a semiconductor laser, and the collimator lens 122, and the detection means 130 are located at the exterior of the case housing 149. Specifically, in the thirteenth embodiment, an optical means 128 for a light source is provided with a mirror 127 and the telecentric scanner 124 for reflecting and deflecting the light beam L, which has been radiated out of the light source device 123, such that the light beam L may enter into the coupler means 110. Also, an optical means 135 for a detection means is provided with a lens 132 and mirrors 133, 134 for guiding the light beam, which has been radiated out of the coupler means 110, to the detection means 130. The optical means 128 for the light source and the optical means 135 for the detection means are accommodated in the optical system case housing 146. The light source device 123 and the detection means 130 are located at the exterior of the case housing 149.

The light source 121 and the detection means 130 are exchanged with new ones in accordance with the kind of the substance to be analyzed and the desired analysis accuracy. Therefore, the light source 121 and the detection means 130 are mounted releasably. For example, in cases where a wide dynamic range is to be obtained, the detection means 130 is replaced by a CCD. In cases where a particularly accurate analysis is to be made, the detection means 130 is replaced by a two-part photodiode. Since the light source device 123 and the detection means 130 are located at the exterior of the case housing 149, they can be very easily exchanged with new ones.

In cases where the light source and the detection means are located in the interior of the optical system case housing 146, since the light source and the detection means must be accommodated within the limited area, the forms of the light source and the detection means are limited. However, in the thirteenth embodiment, wherein the light source and the detection means are located at the exterior of the optical system case housing 146, no limitation is imposed upon the forms of the light source and the detection means, and the light source and the detection means can take on various desired forms. For example, it is possible to employ a plurality of light sources and a plurality of detection means.

Alternatively, a light source, which may be constituted of a semiconductor laser, or the like, may be located at a position independent of the base 147, on which the optical system case housing 146 and the case housing 149 are located. In such cases, the light beam having been produced by the light source may be guided through an optical fiber, particularly a polarization plane keeping type of optical fiber, to the optical means for the light source.

Also, as in the thirteenth embodiment of FIG. 24, the aforesaid eleventh embodiment of FIG. 18 may be modified such that the light source and the detection means may be located at the exterior of the case housing 142. Alternatively, the eleventh embodiment of FIG. 18 may be modified such that the light source may be located at a position independent of the base 140, and the light beam having been produced by the light source may be guided through an optical fiber to the optical means for the light source.

The seventh to thirteenth embodiments described above may be modified such that only either one of the sensor unit relative movement means and the incidence position shifting means may be provided, and analyses may be carried out with respect to a plurality of samples, which are arrayed along a one-dimensional direction.

Fourteenth and fifteenth embodiments of the surface plasmon sensor in accordance with the present invention will be described hereinbelow.

Figure 26:
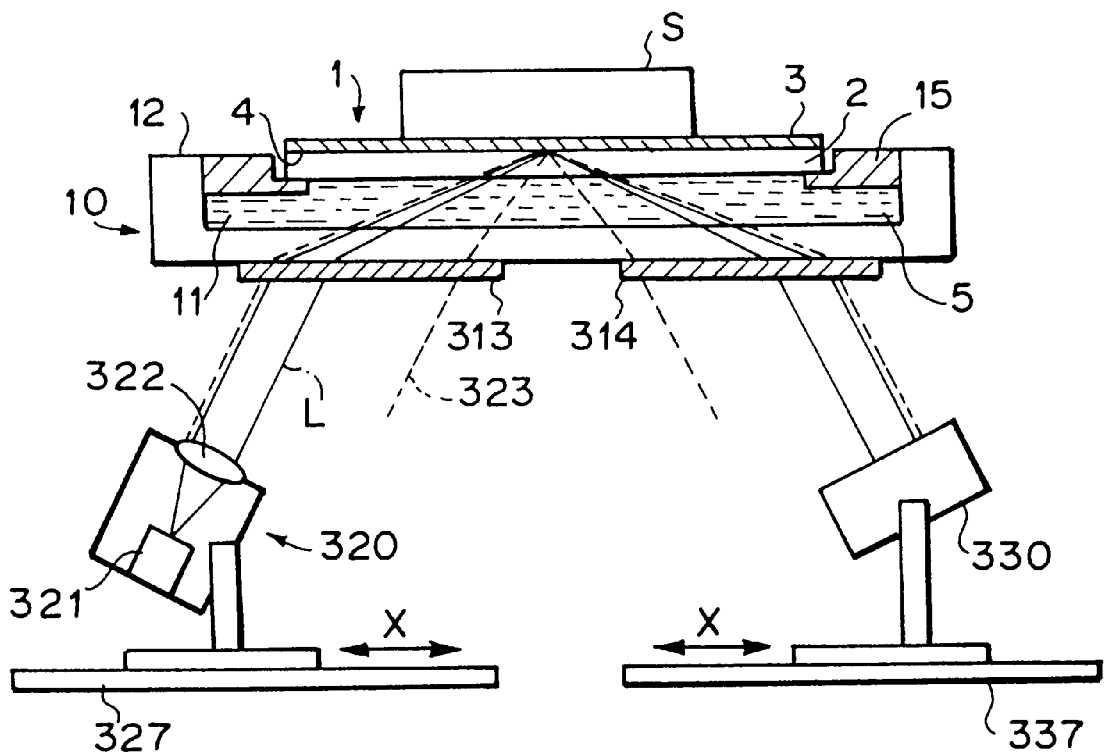
FIG. 26 is a side view showing a fourteenth embodiment of the surface plasmon sensor in accordance with the present invention.

FIG. 26 is a side view showing a fourteenth embodiment of the surface plasmon sensor in accordance with the present invention.

As illustrated in FIG. 26, basically, the surface plasmon sensor comprises the sensor unit 1 provided with the metal film, which is brought into contact with the sample S to be analyzed and may be constituted of gold, silver, or the like. The surface plasmon sensor also comprises the sensor unit support means 15 for supporting the sensor unit 1. The surface plasmon sensor further comprises the coupler means 10, which is located with respect to the sensor unit 1. The matching liquid 5 intervenes between the sensor unit 1 and the coupler means 10. The surface plasmon sensor still further comprises a light-source optical means 320 for producing a light beam and causing the light beam to enter into the coupler means 10, and a photo detecting means 330 for detecting the ATR angle $\theta_{sp}$ from the light beam having been radiated out of the coupler means 10.

The fourteenth embodiment of the surface plasmon sensor in accordance with the present invention will hereinbelow be described in more detail.

The sensor unit 1 comprises the transparent substrate (the sensor substrate) 2, which has uniform thickness and may be constituted of glass, or the like, and the metal film 3, which is formed on the transparent substrate 2 and may be constituted of gold, silver, or the like. In this embodiment, the combination of the metal film 3 and the bonding reaction film (not shown), which is formed on the metal film 3, is referred to as the sensor film.

The coupler means 10 comprises the cell 12, which is constituted of glass and has the recess 11 on the side facing the sensor unit 1, and a light beam entry portion 313 and a light beam radiating portion 314, which are formed on the other side of the cell 12. Each of the light beam entry portion 313 and the light beam radiating portion 314 is constituted of a hologram optical element. The sensor unit support means (the sensor unit attachment) 15 for supporting the sensor unit 1 is located at a portion of the coupler means 10. The sensor unit attachment 15 supports the sensor unit 1 such that the distance between the transparent substrate 2 and the cell 12 may be equal to the predetermined value. The space between the transparent substrate 2 and the coupler means 10 is filled with the matching liquid 5. The transparent substrate 2, the coupler means 10, which is provided with the light beam entry portion 313 and the light beam radiating portion 314 each being constituted of the hologram optical element, and the matching liquid 5 have refractive indexes approximately equal to one another, such that reflection of the light beam from the interfaces among them may be prevented.

The light-source optical means 320 comprises a light source 321, which produces a light beam L and may be constituted of a semiconductor laser, or the like. The light-source optical means 320 also comprises a lens 322 for radiating the light beam L as collimated light. The light-source optical means 320 is located on a stage 327 for a light-source optical means and can be moved in the directions indicated by the double headed arrow X and on the stage 327 for the light-source optical means. The light beam L, which has been produced by the light source 321, is converted by a polarizer (not shown) into P-polarized light and is then caused to enter into the coupler means 10 from the light beam entry portion 313. The light beam L then impinges at a predetermined angle of incidence θ upon the interface 4 between the transparent substrate 2 and the metal film 3. At this time, the angle of incidence θ can be set at various different values by moving the light-source optical means 320 in the directions indicated by the double headed arrow X and on the stage 327 for the light-source optical means. The operation for moving the light-source optical means 320 in the directions indicated by the double headed arrow X is equivalent to the operation for moving the light source 321 in a plane, which is parallel to the interface 4, and in a direction heading towards the focal position of the light beam on the interface 4 or in a direction heading away from the focal position. The angle of incidence θ of the light beam L upon the interface 4 is set so as to vary within an angle range not smaller than the total reflection critical angle, such that the light beam L may be totally reflected from the interface 4.

Figure 27:
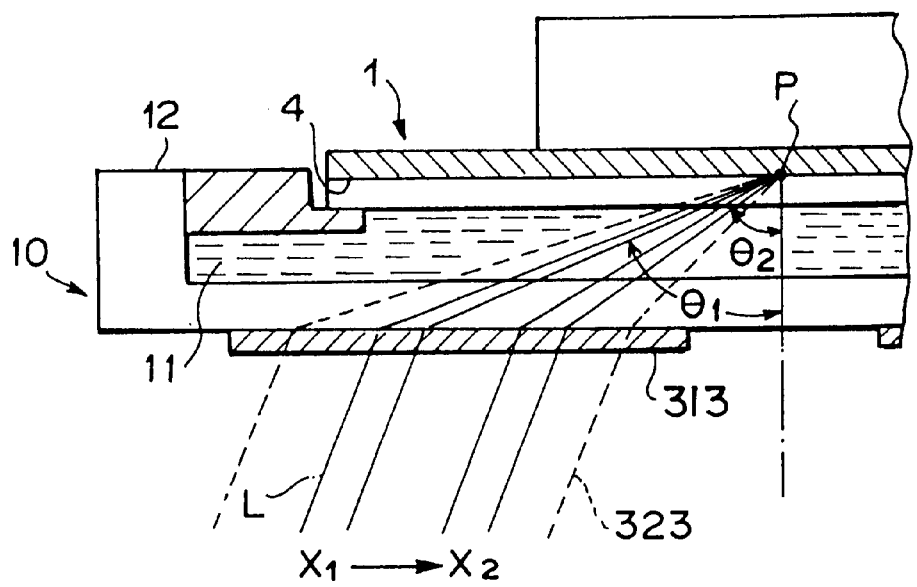
FIG. 27 is an explanatory view showing how a light beam is converged by a hologram optical element.

The hologram optical element, which is employed as each of the light beam entry portion 313 and the light beam radiating portion 314, is designed to have lens functions for converging the light beam and aberration compensating functions and to converge the incident collimated light beam into a single spot. For example, as illustrated in FIG. 27, an optical path, which is indicated by the dotted lines, is set such that the collimated light incident at a predetermined angle may be converged to a predetermined point P on the interface 4. In this manner, every collimated light beam, which impinges upon the light beam entry portion 313 from a different incidence position, is converged to the predetermined point P. Therefore, when the incidence position of the collimated light beam L is shifted from a position $X_1$ to a position $X_2$ in the direction indicated by the arrow in FIG. 27, the angle of incidence of the light beam at the predetermined point P can be changed from $\theta_1$ to $\theta_2$. Accordingly, the light beam can be caused to impinge at various different angles of incidence at the predetermined point P on the interface 4 by merely moving the light-source optical means 320 in parallel.

As the photo detecting means 330, for example, a photodiode, a two-part photodiode proposed in U.S. Ser. No. 08/840,648, a photodiode array, a CCD line sensor, or the like, may be employed. In accordance with a change in incidence position of the light beam L, the position of the light beam L radiated out of the hologram optical element for light beam radiation changes. Therefore, the photo detecting means 330 is located on a stage 337 for the photo detecting means and can be moved in the directions indicated by the double headed arrow X and on the stage 337 for the photo detecting means. The light-source optical means 320 and the photo detecting means 330 are synchronously moved on the stages 327 and 337 and in the direction heading towards each other or in the direction heading away from each other. In this manner, the light beam L, which has been radiated out of the light-source optical means 320 and has then been reflected from the interface 4, can be reliably detected by the photo detecting means 330.

How a sample analysis is carried out in the fourteenth embodiment of the surface plasmon sensor having the constitution described above will be described hereinbelow. The sample S to be analyzed is located such that it may be in contact with the metal film 3. The light beam L, which has been produced and converted into the P-polarized light by the light-source optical means 320, enters into the coupler means 10 from the light beam entry portion 313. The light beam L passes through the coupler means 10 and the matching liquid 5, and impinges upon the interface 4 between the transparent substrate 2 and the metal film 3. As described above, the light-source optical means 320 is moved in the directions indicated by the double headed arrow X and on the stage 327 for the light-source optical means, and the light beam L is thereby caused to impinge at various angles of incidence θ upon the interface 4. The light beam L is then totally reflected from the interface 4 and radiated out of the light beam radiating portion 314. The intensity of the light beam L, which has thus been radiated out of the light beam radiating portion 314, is detected by the photo detecting means 330.

A photo detection signal, which is detected by the photo detecting means 330, represents the intensity I of the totally reflected light beam L with respect to each of the angles of incidence θ upon the interface 4. FIG. 2 approximately shows the relationship between the intensity I of the reflected light beam and the angles of incidence θ.

The light impinging at a specific angle of incidence (i.e., the ATR angle) $θ_{sp}$ upon the interface 4 excites surface plasmon at an interface between the metal film 3 and the sample S. As for the light impinging at the specific angle of incidence $θ_{sp}$ upon the interface 4, the intensity I of the reflected light becomes markedly low. From the photo detection signal detected by the photo detecting means 330, the ATR angle $θ_{sp}$ can be determined. As described above in detail, the specific substance contained in the sample S can be analyzed quantitatively in accordance with the value of the ATR angle $θ_{sp}$.

Figure 28:
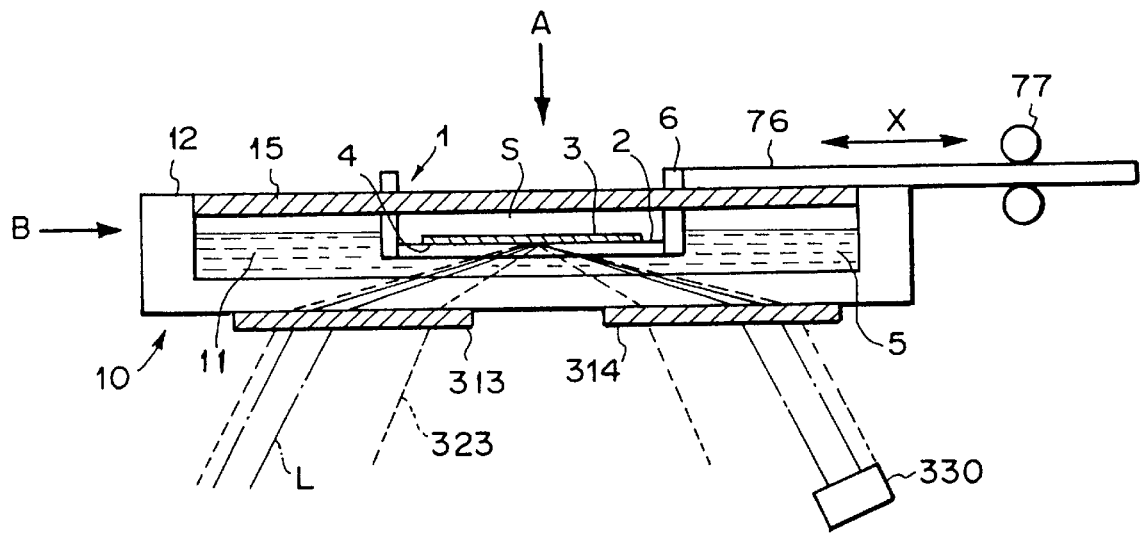
FIG. 28 is a side view showing a fifteenth embodiment of the surface plasmon sensor in accordance with the present invention.
Figure 29:
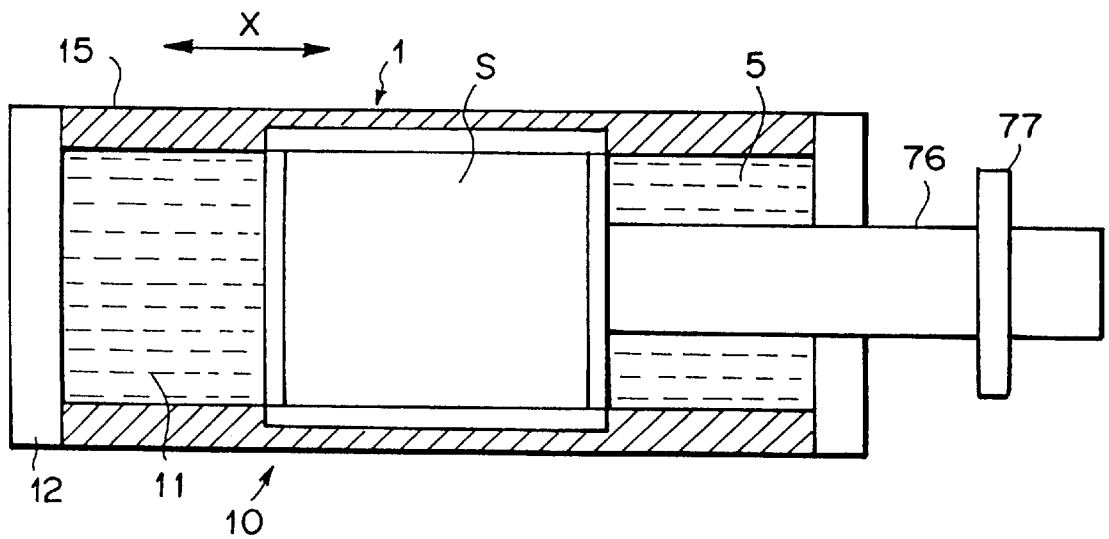
FIG. 29 is a view taken from a direction indicated by the arrow A in FIG. 28.
Figure 30:
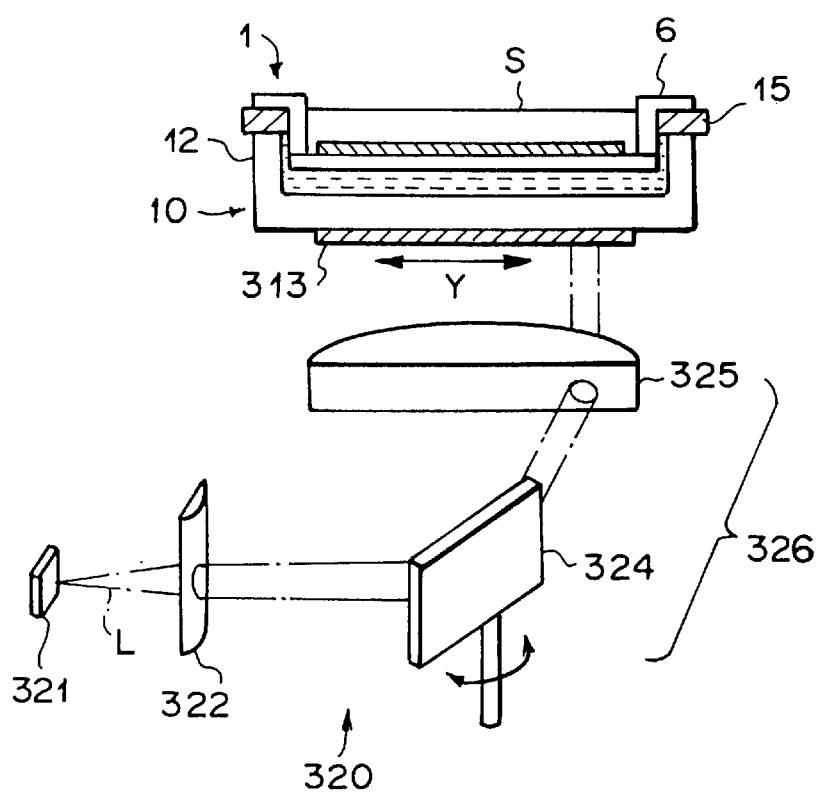
FIG. 30 is a view taken from a direction indicated by the arrow B in FIG. 28.

A fifteenth embodiment of the surface plasmon sensor in accordance with the present invention, which is constituted as a two-dimensional scanning type, will be described hereinbelow. FIG. 28 is a side view showing the fifteenth embodiment of the surface plasmon sensor in accordance with the present invention. FIG. 29 is a view taken from a direction indicated by the arrow A in FIG. 28. FIG. 30 is a view taken from a direction indicated by the arrow B in FIG. 28. However, in FIG. 28, the light-source optical means 320 is not shown. Also, FIG. 30 is a fragmentally sectional view. In the fifteenth embodiment, as for the same constitutions and the same operating sections as those in the aforesaid fourteenth embodiment, detailed explanation will be omitted. Only the different features will be described hereinbelow.

The sensor unit 1 comprises the transparent substrate (the sensor substrate) 2, which has uniform thickness and may be constituted of glass, or the like, and the metal film 3, which is formed on the transparent substrate 2 and may be constituted of gold, silver, or the like. The waterproof wall 6 is formed such that it may surround the metal film 3. When an analysis is to be carried out, the lower portion of the sensor unit 1 is immersed in the matching liquid 5.

As illustrated in FIG. 29, in the fifteenth embodiment, the coupler means 10 has a structure extending in one direction, and the sensor unit attachment 15 is formed along the recess 11 of the coupler means 10. The sensor unit attachment 15 is provided with a conveying rail (not shown), and the sensor unit 1 can be moved along the conveying rail, i.e. along the sensor unit attachment 15. The conveying shaft 76 is secured to the sensor unit 1. Also, the conveying shaft 76 is grasped between the rollers 77, 77 and moved by the rotation of the rollers 77, 77. In accordance with the rotation of the rollers 77, 77, the conveying shaft 76 is moved, and the sensor unit 1 is moved by the conveying shaft 76 in the directions indicated by the double headed arrow X. Specifically, in the fifteenth embodiment, the sensor unit relative movement means is constituted by the conveying rail of the sensor unit attachment 15, the conveying shaft 76, and the rollers 77, 77.

The light-source optical means 320 comprises the light source 321, which produces a light beam L and may be constituted of a semiconductor laser, or the like. The light-source optical means 320 also comprises a cylindrical lens 322 and a telecentric scanner 326, which is a light deflecting means utilizing a telecentric optical system. The telecentric scanner 326 comprises a galvanometer mirror 324, which is located at the position corresponding to the focal length of the cylindrical lens 322, and a cylindrical lens 325. The light beam L, which has been produced by the light source 321, is focalized on the galvanometer mirror 324 by the cylindrical lens 322. The light beam L is then reflected from the galvanometer mirror 324 and impinges upon the cylindrical lens 325 of the telecentric scanner 326. The light beam L is collimated by the cylindrical lens 325 and caused to enter into the coupler means 10 from the light beam entry portion 313. In this embodiment, the hologram optical element, which constitutes each of the light beam entry portion 313 and the light beam radiating portion 314, has the cylindrical lens functions and the aberration compensating functions. The light beam, which has been entered into the coupler means 10 from the light beam entry portion 313 is converged in one direction on the interface 4 between the metal film 3 and the transparent substrate 2. In this embodiment, the hologram optical element has the cylindrical lens functions having the refracting power only in the plane, which is parallel to the plane of the sheet of FIG. 28. The direction, which is normal to the plane of the sheet of FIG. 28, is the axial direction of the cylindrical lens functions. The axial direction of the cylindrical lens functions is the same as the directions indicated by the double headed arrow Y in FIG. 30. In accordance with the swinging operation of the galvanometer mirror 324, the position of incidence of the light beam L upon the light beam entry portion 313 is shifted in parallel along the directions indicated by the double headed arrow Y.

In the fifteenth embodiment of FIG. 28, as described above, the telecentric scanner 326, which is the light deflecting means, is employed as the means for shifting the incidence position of the light beam L. Alternatively, for example, the incidence position shifting means may be constituted such that the stage 327 for the light-source optical means, on which the light-source optical means 320 has been located, may be located on a stage, which can be moved in the directions indicated by the double headed arrow Y. The stage 327 may thus be moved in the directions indicated by the double headed arrow Y, and the incidence position of the light beam may thereby be shifted in parallel along the directions indicated by the double headed arrow Y.

The location of the photo detecting means 330 is regulated such that it can reliably detect the light beam, which has been reflected from the interface 4 and has then been radiated out of the light beam radiating portion 314.

How the sample analyses are carried out in the fifteenth embodiment of the surface plasmon sensor having the constitution described above will be described hereinbelow. Firstly, as illustrated in FIG. 11A, a plurality of sample cells 8, 8, . . . , which respectively contain different samples $S_1$, $S_2$, $S_3$, . . . , are located on the sensor film. The samples Sn (n=1, 2, 3, . . . ) are thus located such that they may be in contact with the sensor film.

In the fifteenth embodiment, the sensor unit 1 is intermittently conveyed along the conveying rail of the sensor unit attachment 15 and in the directions indicated by the double headed arrow X. Also, with the telecentric scanner 326, the light beam L is shifted in parallel in the directions indicated by the double headed arrow Y. The light beam L is thus caused to impinge successively upon the portions of the interface 4, which correspond to the samples Sn. In this manner, the analyses are carried out with respect to the respective samples. The analysis with respect to each sample is carried out in the manner described below. Specifically, in the same manner as that in the aforesaid fourteenth embodiment of FIG. 26, the light-source optical means 320 is moved in the directions indicated by the double headed arrow X and on the stage 327 for the light-source optical means, and the light beam L is thereby caused to impinge at various angles of incidence upon the portion of the interface 4, which corresponds to each sample. Also, the intensity of the light beam L, which has thus been totally reflected from the interface 4 and radiated out of the light beam radiating portion 314, is detected by the photo detecting means 330. The two-dimensional scanning is thus carried out such that the light beam L may be irradiated under the same conditions with respect to the samples Sn. In this manner, the analyses of the plurality of the samples Sn can be carried out quickly and efficiently.

As described above, in the fifteenth embodiment, the two-dimensional scanning with the light beam L can be carried out. Therefore, the fifteenth embodiment is also applicable when, for example, a sample, such as a gel sheet having been used in electrophoresis, is located on the metal film 3 and scanned in two-dimensional directions, and two-dimensional information representing the physical properties of a substance, which is to be analyzed and is distributed in the sample, is thereby obtained.

Also, as illustrated in FIG. 12, a plurality of regions 3a, 3a, . . . may be set on the metal film 3, and sensor films provided with different bonding reaction films may be employed for the regions 3a, 3a, . . . In this condition, the two-dimensional scanning with the light beam may be carried out. In this manner, analyses of different immune reactions, and the like, which occur in the respective regions, can be carried out with respect to the respective regions.

The fifteenth embodiment described above may be modified such that only either one of the sensor unit relative movement means and the incidence position shifting means may be provided, and analyses may be carried out with respect to a plurality of samples, which are arrayed along a one-dimensional direction.

What is claimed is:

1. A surface plasmon sensor, comprising:
    i) a sensor unit provided with a transparent substrate, which has a predetermined refractive index, and a metal film, which is located on one surface side of said transparent substrate, and
    ii) a coupler means located on the other surface side of said transparent substrate, which surface side is opposite to said one surface, with a refractive index matching liquid, which has a refractive index approximately equal to said predetermined refractive index, intervening between said transparent substrate and said coupler means,
        said coupler means having a light beam entry portion, which is formed at a portion of said coupler means, and a light beam radiating portion, which is formed at a different portion of said coupler means, such that said coupler means transmit a light beam having been entered from said light beam entry portion, cause the transmitted light beam to impinge upon an interface between said transparent substrate and said metal film, transmit the light beam having been totally reflected from said interface, and then radiate the totally reflected light beam out of said light beam radiating portion, portions of said coupler means, which transmit the light beam, having a refractive index approximately equal to said predetermined refractive index,
        the surface plasmon sensor causing the light beam to enter from said light beam entry portion and detecting an attenuated total reflection angle $\theta_{sp}$ from the light beam, which has been totally reflected from said interface and has then been radiated out of said light beam radiating portion,
        wherein a sensor unit support means is provided, said sensor unit support means supporting said sensor unit such that a distance between said transparent substrate and said coupler means be kept to be equal to a predetermined value, and
        wherein the space between said transparent substrate and said coupler means is filled with said refractive index matching liquid.

2. A surface plasmon sensor as defined in claim 1 wherein said sensor unit support means is secured to a portion of said coupler means.

3. A surface plasmon sensor as defined in claim 1 wherein the surface plasmon sensor further comprises a matching liquid supply means, which supplies said refractive index matching liquid into said space, and
    a vacant member, which communicates with said space and allows said refractive index matching liquid to be introduced up to a position higher than said other surface of said transparent substrate,
    said refractive index matching liquid being filled in said space by said matching liquid supply means.

4. A surface plasmon sensor as defined in claim 1 wherein a liquid reservoir for storing said refractive index matching liquid therein is formed on the side of said coupler means, which side stands facing said transparent substrate,
    said transparent substrate is provided with a waterproof wall, which surrounds said metal film, and said sensor unit is supported in said liquid reservoir such that said other surface of said transparent substrate may be immersed in said refractive index matching liquid.

5. A surface plasmon sensor as defined in claim 1 wherein said coupler means is provided with a prism, and said light beam entry portion and said light beam radiating portion are formed in said prism.

6. A surface plasmon sensor as defined in claim 1 wherein each of said light beam entry portion and said light beam radiating portion of said coupler means is constituted of a diffraction grating.

7. A surface plasmon sensor as defined in claim 1 wherein said coupler means is provided with a convex portion on the side of said coupler means, which side is opposite to the side facing said transparent substrate, each of one lateral face of said convex portion and the other lateral face thereof, which is opposite to said one lateral face, is constituted of a transparent plate, the region inside of said convex portion being filled with said refractive index matching liquid, and said one lateral face and said other lateral face of said convex portion respectively serve as said light beam entry portion and said light beam radiating portion.

8. A surface plasmon sensor as defined in claim 1 wherein said transparent substrate of said sensor unit is constituted of a main transparent substrate and a supporting transparent substrate, which have said predetermined refractive index and are in close contact with each other, said metal film is located on said main transparent substrate, and said supporting transparent substrate is located such that it stand facing said coupler means with said refractive index matching liquid intervening therebetween.

9. A surface plasmon sensor as defined in claim 8 wherein said main transparent substrate and said supporting transparent substrate are in close contact with each other via a refractive index matching liquid, which has a refractive index approximately equal to said predetermined refractive index.

10. A surface plasmon sensor as defined in claim 1 wherein a bonding reaction film is located on said metal film, and the surface plasmon sensor detects a specific substance, which is capable of undergoing a bonding reaction with said bonding reaction film.

11. A surface plasmon sensor, comprising:

i) a sensor unit provided with a transparent substrate, which has a predetermined refractive index, and a metal film, which is located on one surface side of said transparent substrate, and ii) a coupler means located on the other surface side of said transparent substrate, which surface side is opposite to said one surface, with a refractive index matching liquid, which has a refractive index approximately equal to said predetermined refractive index, intervening between said transparent substrate and said coupler means, said coupler means having a light beam entry portion, which is formed at a portion of said coupler means, and a light beam radiating portion, which is formed at a different portion of said coupler means, such that said coupler means transmit a light beam having been entered from said light beam entry portion, cause the transmitted light beam to impinge upon an interface between said transparent substrate and said metal film, transmit the light beam having been totally reflected from said interface, and then radiate the totally reflected light beam out of said light beam radiating portion, portions of said coupler means, which transmit the light beam, having a refractive index approximately equal to said predetermined refractive index, the surface plasmon sensor causing the light beam to enter from said light beam entry portion and detecting an attenuated total reflection angle $\theta_{sp}$ from the light beam, which has been totally reflected from said interface and has then been radiated out of said light beam radiating portion, wherein a sensor unit support means is provided, said sensor unit support means supporting said sensor unit such that a distance between said transparent substrate and said coupler means be kept to be equal to a predetermined value, wherein the space between said transparent substrate and said coupler means is filled with said refractive index matching liquid, and wherein the surface plasmon sensor further comprises either one or both of an incidence position shifting means and a sensor unit relative movement means, said incidence position shifting means shifting the incidence position of the light beam at said light beam entry portion such that the light beam successively impinge upon different portions of said interface, which are taken along a predetermined direction, and under the same incidence conditions, said sensor unit relative movement means moving said sensor unit with respect to said coupler means and along a predetermined direction such that said distance between said transparent substrate and said coupler means be kept to be equal to the predetermined value.

12. A surface plasmon sensor as defined in claim 11 wherein the surface plasmon sensor comprises both of said incidence position shifting means and said sensor unit relative movement means, and said predetermined direction, along which said different portions of said interface are taken in the shifting operation carried out by said incidence position shifting means, and said predetermined direction, along which said sensor unit is moved with respect to said coupler means by said sensor unit relative movement means, intersect with each other.

13. A surface plasmon sensor as defined in claim 11 wherein said incidence position shifting means is a telecentric scanning optical system.

14. A surface plasmon sensor as defined in claim 11 wherein said sensor unit support means is secured to a portion of said coupler means.

15. A surface plasmon sensor as defined in claim 11 wherein a light-source optical means for producing the light beam and causing the light beam to enter into said light beam entry portion, a detection means for detecting an attenuated total reflection angle $\theta_{sp}$ from the light beam having been radiated out of said light beam radiating portion, and said coupler means are located on a base, said sensor unit support means is located on said base and secured thereto, said sensor unit is supported by said sensor unit support means such that said sensor unit can be moved with respect to said coupler means, and said sensor unit relative movement means moves said sensor unit.

16. A surface plasmon sensor as defined in claim 11 wherein said sensor unit support means is located on a base and secured thereto, said sensor unit is fixedly supported by said sensor unit support means, an optical system unit is located on said base such that said optical system unit can be moved with respect to said sensor unit, said optical system unit comprising a light-source optical means for producing the light beam and causing the light beam to enter into said light beam entry portion, a detection means for detecting an attenuated total reflection angle $\theta_{sp}$ from the light beam having been radiated out of said light beam radiating portion, and said coupler means, and said sensor unit relative movement means moves said optical system unit.

17. A surface plasmon sensor as defined in claim 11 wherein said sensor unit support means is located on a base and secured thereto, said sensor unit is supported by said sensor unit support means such that said sensor unit can be moved with respect to said coupler means, said sensor unit relative movement means moves said sensor unit, an optical system unit is located on said base, said optical system unit comprising an optical means for a light source, which optical means causes the light beam to enter into said light beam entry portion, an optical means for a detection means, which optical means guides the light beam to the detection means for detecting an attenuated total reflection angle $\theta_{sp}$ from the light beam having been radiated out of said light beam radiating portion, and said coupler means, and the light source for producing the light beam and said detection means are releasably located on said base and at positions independent of said optical system unit.

18. A surface plasmon sensor as defined in claim 11 wherein said sensor unit support means is located on a base and secured thereto, said sensor unit is fixedly supported by said sensor unit support means, an optical system unit is located on said base such that said optical system unit can be moved with respect to said sensor unit, said optical system unit comprising an optical means for a light source, which optical means causes the light beam to enter into said light beam entry portion, an optical means for a detection means, which optical means guides the light beam to the detection means for detecting an attenuated total reflection angle $\theta_{sp}$ from the light beam having been radiated out of said light beam radiating portion, and said coupler means, said sensor unit relative movement means moves said optical system unit, and the light source for producing the light beam and said detection means are releasably located on said base and at positions independent of said optical system unit.

19. A surface plasmon sensor as defined in claim 11 wherein said sensor unit support means is located on a base and secured thereto, said sensor unit is supported by said sensor unit support means such that said sensor unit can be moved with respect to said coupler means, said sensor unit relative movement means moves said sensor unit, an optical system unit is located on said base, said optical system unit comprising an optical means for a light source, which optical means causes the light beam to enter into said light beam entry portion, a detection means for detecting an attenuated total reflection angle $\theta_{sp}$ from the light beam having been radiated out of said light beam radiating portion, and said coupler means, and the light source for producing the light beam is independently located at the exterior of said base.

20. A surface plasmon sensor as defined in claim 11 wherein said sensor unit support means is located on a base and secured thereto, said sensor unit is fixedly supported by said sensor unit support means, an optical system unit is located on said base such that said optical system unit can be moved with respect to said sensor unit, said optical system unit comprising an optical means for a light source, which optical means causes the light beam to enter into said light beam entry portion, a detection means for detecting an attenuated total reflection angle $\theta_{sp}$ from the light beam having been radiated out of said light beam radiating portion, and said coupler means, said sensor unit relative movement means moves said optical system unit, and the light source for producing the light beam is independently located at the exterior of said base.

21. A surface plasmon sensor as defined in claim 19 wherein the surface plasmon sensor is provided with an optical fiber for guiding the light beam, which has been produced by said light source, to said optical means for the light source.

22. A surface plasmon sensor as defined in claim 20 wherein the surface plasmon sensor is provided with an optical fiber for guiding the light beam, which has been produced by said light source, to said optical means for the light source.

23. A surface plasmon sensor as defined in claim 21 wherein said optical fiber is a polarization plane keeping type of optical fiber.

24. A surface plasmon sensor as defined in claim 22 wherein said optical fiber is a polarization plane keeping type of optical fiber.

25. A surface plasmon sensor as defined in claim 11 wherein the surface plasmon sensor further comprises a matching liquid supply means, which supplies said refractive index matching liquid into said space, and a vacant member, which communicates with said space and allows said refractive index matching liquid to be introduced up to a position higher than said other surface of said transparent substrate, said refractive index matching liquid being filled in said space by said matching liquid supply means.

26. A surface plasmon sensor as defined in claim 11 wherein a liquid reservoir for storing said refractive index matching liquid therein is formed on the side of said coupler means, which side stands facing said transparent substrate, said transparent substrate is provided with a waterproof wall, which surrounds said metal film, and said sensor unit is supported in said liquid reservoir such that said other surface of said transparent substrate be immersed in said refractive index matching liquid.

27. A surface plasmon sensor as defined in claim 11 wherein said coupler means is provided with a prism, and said light beam entry portion and said light beam radiating portion are formed in said prism.

28. A surface plasmon sensor as defined in claim 11 wherein each of said light beam entry portion and said light beam radiating portion of said coupler means is constituted of a diffraction grating.

29. A surface plasmon sensor as defined in claim 11 wherein said coupler means is provided with a convex portion on the side of said coupler means, which side is opposite to the side facing said transparent substrate, each of one lateral face of said convex portion and the other lateral face thereof, which is opposite to said one lateral face, is constituted of a transparent plate, the region inside of said convex portion being filled with said refractive index matching liquid, and said one lateral face and said other lateral face of said convex portion respectively serve as said light beam entry portion and said light beam radiating portion.

30. A surface plasmon sensor as defined in claim 11 wherein said transparent substrate of said sensor unit is constituted of a supporting transparent substrate and a main transparent substrate, which is located on said supporting transparent substrate, said metal film is located on said main transparent substrate, and said supporting transparent substrate is located such that it stand facing said coupler means with said refractive index matching liquid intervening therebetween.

31. A surface plasmon sensor as defined in claim 11 wherein a bonding reaction film is located on said metal film, and the surface plasmon sensor detects a specific substance, which is capable of undergoing a bonding reaction with said bonding reaction film.

32. A surface plasmon sensor as defined in claim 11 wherein different kinds of bonding reaction films are located at different positions on said metal film, and the surface plasmon sensor detects a specific substance, which is capable of undergoing a bonding reaction with each of said bonding reaction films.

33. A surface plasmon sensor as defined in claim 11 wherein said transparent substrate of said sensor unit is constituted of a supporting transparent substrate and a plurality of main transparent substrates, which are located at different positions on said supporting transparent substrate, metal films are located respectively on the plurality of said main transparent substrates, and said supporting transparent substrate is located such that it stand facing said coupler means with said refractive index matching liquid intervening therebetween.

34. A surface plasmon sensor as defined in claim 33 wherein the plurality of said main transparent substrates have different substrate sizes.

35. A surface plasmon sensor as defined in claim 33 wherein bonding reaction films are located respectively on said metal films, each of which is located on one of said main transparent substrates, and the surface plasmon sensor detects a specific substance, which is capable of undergoing a bonding reaction with each of said bonding reaction films.

36. A surface plasmon sensor as defined in claim 35 wherein said bonding reaction films are different kinds of reaction films.

37. A surface plasmon sensor as defined in claim 30 wherein said supporting transparent substrate and said main transparent substrate are in close contact with each other via a refractive index matching liquid, which has a refractive index approximately equal to said predetermined refractive index.

38. A surface plasmon sensor as defined in claim 33 wherein said supporting transparent substrate and each of said main transparent substrates are in close contact with each other via a refractive index matching liquid, which has a refractive index approximately equal to said predetermined refractive index.

39. A surface plasmon sensor as defined in claim 30 wherein said main transparent substrate is releasably located on said supporting transparent substrate.

40. A surface plasmon sensor as defined in claim 33 wherein said main transparent substrates are releasably located on said supporting transparent substrate.

41. A surface plasmon sensor, comprising:

i) a sensor unit provided with a transparent substrate, which has a predetermined refractive index, and a metal film, which is located on one surface side of said transparent substrate and brought into contact with a sample, ii) a coupler means located on the other surface side of said transparent substrate, which surface side is opposite to said one surface, with a refractive index matching liquid, which has a refractive index approximately equal to said predetermined refractive index, intervening between said transparent substrate and said coupler means, said coupler means having a light beam entry portion, which is formed at a portion of said coupler means, and a light beam radiating portion, which is formed at a different portion of said coupler means, such that said coupler means transmit a light beam having been entered from said light beam entry portion, cause the transmitted light beam to impinge upon an interface between said transparent substrate and said metal film, transmit the light beam having been totally reflected from said interface, and then radiate the totally reflected light beam out of said light beam radiating portion, portions of said coupler means, which transmit the light beam, having a refractive index approximately equal to said predetermined refractive index, and iii) a light source for producing the light beam, the surface plasmon sensor collimating the light beam, which has been produced by said light source, causing the collimated light beam to enter from said light beam entry portion, and detecting an attenuated total reflection angle $\theta_{sp}$ from the light beam, which has been totally reflected from said interface and has then been radiated out of said light beam radiating portion, wherein each of said light beam entry portion and said light beam radiating portion is constituted of a hologram optical element.

42. A surface plasmon sensor as defined in claim 41 wherein said hologram optical element is designed to converge the incident collimated light beam to a predetermined position, a light source moving means is provided, said light source moving means moving said light source in a plane, which is parallel to said interface, and in a direction heading towards said predetermined position or in a direction heading away from said predetermined position, and said light source is moved, whereby the light beam is caused to enter from different positions on said light beam entry portion and caused to impinge upon said interface at various different angles of incidence and at said predetermined position.

43. A surface plasmon sensor as defined in claim 42 wherein said hologram optical element has lens functions and aberration compensating functions, and the light beam is converged to said predetermined position by said lens functions and said aberration compensating functions.

44. A surface plasmon sensor as defined in claim 42 wherein said hologram optical element has cylindrical lens functions and aberration compensating functions, and the light beam is converged to said predetermined position by said cylindrical lens functions and said aberration compensating functions.

45. A surface plasmon sensor as defined in claim 44 wherein the surface plasmon sensor further comprises a position regulating means for regulating the position of said sensor unit such that a distance between said transparent substrate and said coupler means be kept to be equal to a predetermined value, and a sensor unit moving means for moving said sensor unit in a predetermined direction, the space between said transparent substrate and said coupler means being filled with said refractive index matching liquid.

46. A surface plasmon sensor as defined in claim 44 wherein the surface plasmon sensor further comprises an incidence position shifting means for shifting the incidence position of the light beam at said light beam entry portion such that the light beam may successively impinge upon different portions of said interface, which are taken along the same direction as an axial direction of said cylindrical lens functions.

* * * * *